US009089972B2

(12) United States Patent
Stuart et al.

(10) Patent No.: US 9,089,972 B2
(45) Date of Patent: *Jul. 28, 2015

(54) REMOTE PRESENCE SYSTEM INCLUDING A CART THAT SUPPORTS A ROBOT FACE AND AN OVERHEAD CAMERA

(71) Applicant: INTOUCH TECHNOLOGIES, INC., Goleta, CA (US)

(72) Inventors: David Stuart, Santa Barbara, CA (US); Daniel Steven Sanchez, Summerland, CA (US); Fuji Lai, Goleta, CA (US); Kevin Hanrahan, Santa Barbara, CA (US); Charles S. Jordan, Santa Barbara, CA (US); David Roe, Santa Barbara, CA (US); James Rosenthal, Santa Barbara, CA (US); Amante Mangaser, Goleta, CA (US); Blair Whitney, Santa Barbara, CA (US); Derek Walters, Goleta, CA (US)

(73) Assignee: INTOUCH TECHNOLOGIES, INC., Goleta, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/157,470

(22) Filed: Jan. 16, 2014

(65) Prior Publication Data
US 2014/0135990 A1 May 15, 2014

Related U.S. Application Data

(63) Continuation of application No. 12/717,806, filed on Mar. 4, 2010, now Pat. No. 8,670,017.

(51) Int. Cl.
*G05B 15/00* (2006.01)
*B25J 9/16* (2006.01)
(Continued)

(52) U.S. Cl.
CPC .......... *B25J 9/1697* (2013.01); *G06F 19/3418* (2013.01); *H04N 7/185* (2013.01); *G06F 19/321* (2013.01)

(58) Field of Classification Search
CPC ..... B25J 9/1697; G06F 19/3418; H04N 7/185
USPC ............ 29/407.04, 450; 244/3.15; 348/14.05, 348/87, 135, 143, 14.16, 86; 381/122; 382/153; 700/247, 250, 259, 260; 705/2, 400, 1.1, 14.16; 706/11
See application file for complete search history.

(56) References Cited

U.S. PATENT DOCUMENTS 3,821,995 A 7/1974 Aghnides
4,107,689 A 8/1978 Jellinek
(Continued)

FOREIGN PATENT DOCUMENTS

AU 1216200 A 5/2000
CA 2289697 A1 11/1998
(Continued)

OTHER PUBLICATIONS

Oh et al., "Autonomous Battery Recharging for Indoor Mobile Robots", Proceedings of Australian Conference on Robotics and Automation, 2000, pp. 1-6.
(Continued)

*Primary Examiner* — Gerald Gauthier

(57) ABSTRACT

A tele-presence system that includes a cart. The cart includes a robot face that has a robot monitor, a robot camera, a robot speaker, a robot microphone, and an overhead camera. The system also includes a remote station that is coupled to the robot face and the overhead camera. The remote station includes a station monitor, a station camera, a station speaker and a station microphone. The remote station can display video images captured by the robot camera and/or overhead camera. By way of example, the cart can be used in an operating room, wherein the overhead camera can be placed in a sterile field and the robot face can be used in a non-sterile field. The user at the remote station can conduct a teleconference through the robot face and also obtain a view of a medical procedure through the overhead camera.

30 Claims, 5 Drawing Sheets

(51) Int. Cl.
*H04N 7/18* (2006.01)
*G06F 19/00* (2011.01)

(56) References Cited

U.S. PATENT DOCUMENTS

| | | |
|---|---|---|
| 4,213,182 A | 7/1980 | Eichelberger et al. |
| 4,413,693 A | 11/1983 | Derby |
| 4,471,354 A | 9/1984 | Smith |
| 4,519,466 A | 5/1985 | Shiraishi |
| 4,553,309 A * | 11/1985 | Hess et al. .................. 29/450 |
| 4,572,594 A | 2/1986 | Schwartz |
| 4,625,274 A | 11/1986 | Schroeder |
| 4,638,445 A | 1/1987 | Mattaboni |
| 4,652,204 A | 3/1987 | Arnett |
| 4,669,168 A | 6/1987 | Tamura et al. |
| 4,679,152 A | 7/1987 | Perdue |
| 4,697,278 A | 9/1987 | Fleischer |
| 4,697,472 A | 10/1987 | Hiyane |
| 4,709,265 A | 11/1987 | Silverman et al. |
| 4,733,737 A | 3/1988 | Falamak |
| 4,751,658 A | 6/1988 | Kadonoff et al. |
| 4,766,581 A | 8/1988 | Korn et al. |
| 4,777,416 A | 10/1988 | George, II et al. |
| 4,797,557 A | 1/1989 | Ohman |
| 4,803,625 A | 2/1989 | Fu et al. |
| 4,847,764 A | 7/1989 | Halvorson |
| 4,875,172 A | 10/1989 | Kanayama |
| 4,878,501 A | 11/1989 | Shue |
| 4,942,512 A | 7/1990 | Kohno |
| 4,942,538 A | 7/1990 | Yuan et al. |
| 4,953,159 A | 8/1990 | Hayden et al. |
| 4,974,607 A | 12/1990 | Miwa |
| 4,977,971 A | 12/1990 | Crane, III et al. |
| 5,006,988 A | 4/1991 | Borenstein et al. |
| 5,040,116 A | 8/1991 | Evans, Jr. et al. |
| 5,051,906 A | 9/1991 | Evans, Jr. et al. |
| 5,073,749 A | 12/1991 | Kanayama |
| 5,084,828 A | 1/1992 | Kaufman et al. |
| 5,130,794 A | 7/1992 | Ritchey |
| 5,148,591 A | 9/1992 | Pryor |
| 5,153,833 A | 10/1992 | Gordon et al. |
| 5,155,684 A | 10/1992 | Burke et al. |
| 5,157,491 A | 10/1992 | Kassatly |
| 5,182,641 A | 1/1993 | Diner et al. |
| 5,186,270 A | 2/1993 | West |
| 5,193,143 A | 3/1993 | Kaemmerer et al. |
| 5,217,453 A | 6/1993 | Wilk |
| 5,220,263 A | 6/1993 | Onishi et al. |
| 5,224,157 A | 6/1993 | Yamada et al. |
| 5,230,023 A | 7/1993 | Nakano |
| 5,231,693 A | 7/1993 | Backes et al. |
| 5,236,432 A | 8/1993 | Matsen, III et al. |
| 5,262,944 A | 11/1993 | Weisner et al. |
| 5,305,427 A | 4/1994 | Nagata |
| 5,315,287 A | 5/1994 | Sol |
| 5,319,611 A | 6/1994 | Korba |
| 5,341,242 A | 8/1994 | Gilboa et al. |
| 5,341,459 A | 8/1994 | Backes |
| 5,341,854 A | 8/1994 | Zezulka et al. |
| 5,347,306 A | 9/1994 | Nitta |
| 5,347,457 A | 9/1994 | Tanaka et al. |
| 5,350,033 A | 9/1994 | Kraft |
| 5,366,896 A | 11/1994 | Margrey et al. |
| 5,374,879 A | 12/1994 | Pin et al. |
| 5,375,195 A | 12/1994 | Johnston |
| 5,400,068 A | 3/1995 | Ishida et al. |
| 5,413,693 A | 5/1995 | Redepenning |
| 5,417,210 A | 5/1995 | Funda et al. |
| 5,419,008 A | 5/1995 | West |
| 5,436,542 A | 7/1995 | Petelin et al. |
| 5,441,042 A | 8/1995 | Putman |
| 5,441,047 A | 8/1995 | David et al. |
| 5,442,728 A | 8/1995 | Kaufman et al. |
| 5,462,051 A | 10/1995 | Oka et al. |
| 5,486,853 A | 1/1996 | Baxter et al. |
| 5,510,832 A | 4/1996 | Garcia |
| 5,511,147 A | 4/1996 | Abdel-Malek |
| 5,528,289 A | 6/1996 | Cortjens et al. |
| 5,539,741 A | 7/1996 | Barraclough et al. |
| 5,544,649 A | 8/1996 | David et al. |
| 5,550,577 A | 8/1996 | Verbiest et al. |
| 5,553,609 A | 9/1996 | Chen et al. |
| 5,563,998 A | 10/1996 | Yaksich et al. |
| 5,572,229 A | 11/1996 | Fisher |
| 5,572,999 A | 11/1996 | Funda et al. |
| 5,594,859 A | 1/1997 | Palmer et al. |
| 5,600,573 A | 2/1997 | Hendricks et al. |
| 5,617,539 A | 4/1997 | Ludwig et al. |
| 5,619,341 A | 4/1997 | Auyeung et al. |
| 5,623,679 A | 4/1997 | Rivette et al. |
| 5,630,566 A | 5/1997 | Case |
| 5,636,218 A | 6/1997 | Ishikawa et al. |
| 5,652,849 A | 7/1997 | Conway et al. |
| 5,657,246 A | 8/1997 | Hogan et al. |
| 5,659,779 A | 8/1997 | Laird et al. |
| 5,673,082 A | 9/1997 | Wells et al. |
| 5,675,229 A | 10/1997 | Thorne |
| 5,682,199 A | 10/1997 | Lankford |
| 5,684,695 A | 11/1997 | Bauer |
| 5,701,904 A | 12/1997 | Simmons et al. |
| 5,734,805 A | 3/1998 | Isensee et al. |
| 5,739,657 A | 4/1998 | Takayama et al. |
| 5,748,629 A | 5/1998 | Caldara et al. |
| 5,749,058 A | 5/1998 | Hashimoto |
| 5,749,362 A | 5/1998 | Funda et al. |
| 5,754,631 A | 5/1998 | Cave |
| 5,758,079 A | 5/1998 | Ludwig et al. |
| 5,762,458 A | 6/1998 | Wang et al. |
| 5,764,731 A | 6/1998 | Yablon |
| 5,767,897 A | 6/1998 | Howell |
| 5,786,846 A | 7/1998 | Hiroaki |
| 5,787,545 A | 8/1998 | Colens |
| 5,793,365 A | 8/1998 | Tang et al. |
| 5,801,755 A | 9/1998 | Echerer |
| 5,802,494 A | 9/1998 | Kuno |
| 5,836,872 A | 11/1998 | Kenet et al. |
| 5,838,575 A | 11/1998 | Lion |
| 5,844,599 A | 12/1998 | Hildin |
| 5,857,534 A | 1/1999 | DeVault et al. |
| 5,867,653 A | 2/1999 | Aras et al. |
| 5,871,451 A | 2/1999 | Unger et al. |
| 5,872,922 A | 2/1999 | Hogan et al. |
| 5,876,325 A | 3/1999 | Mizuno et al. |
| 5,911,036 A | 6/1999 | Wright et al. |
| 5,917,958 A | 6/1999 | Nunally et al. |
| 5,927,423 A | 7/1999 | Wada et al. |
| 5,949,758 A | 9/1999 | Kober |
| 5,954,692 A | 9/1999 | Smith et al. |
| 5,959,423 A | 9/1999 | Nakanishi et al. |
| 5,961,446 A | 10/1999 | Beller et al. |
| 5,966,130 A | 10/1999 | Benman, Jr. |
| 5,973,724 A | 10/1999 | Riddle |
| 5,974,446 A | 10/1999 | Sonnenreich et al. |
| 5,983,263 A | 11/1999 | Rothrock et al. |
| 5,995,119 A | 11/1999 | Cosatto et al. |
| 5,995,884 A | 11/1999 | Allen et al. |
| 5,999,977 A | 12/1999 | Riddle |
| 6,006,946 A | 12/1999 | Williams et al. |
| 6,031,845 A | 2/2000 | Walding |
| 6,036,812 A | 3/2000 | Williams et al. |
| 6,047,259 A | 4/2000 | Campbell et al. |
| 6,091,219 A | 7/2000 | Maruo et al. |
| 6,113,343 A | 9/2000 | Goldenberg et al. |
| 6,133,944 A | 10/2000 | Braun et al. |
| 6,135,228 A | 10/2000 | Asada et al. |
| 6,148,100 A | 11/2000 | Anderson et al. |
| 6,160,582 A | 12/2000 | Hill |
| 6,170,929 B1 | 1/2001 | Wilson et al. |
| 6,175,779 B1 | 1/2001 | Barrett |
| 6,189,034 B1 | 2/2001 | Riddle |
| 6,201,984 B1 | 3/2001 | Funda et al. |
| 6,211,903 B1 | 4/2001 | Bullister |
| 6,219,587 B1 | 4/2001 | Ahlin et al. |
| 6,232,735 B1 | 5/2001 | Baba et al. |

(56) References Cited

U.S. PATENT DOCUMENTS

| | | |
|---|---|---|
| 6,233,504 B1 | 5/2001 | Das et al. |
| 6,233,735 B1 | 5/2001 | Ebihara |
| 6,250,928 B1 | 6/2001 | Poggio et al. |
| 6,256,556 B1 | 7/2001 | Zenke |
| 6,259,806 B1 | 7/2001 | Green |
| 6,259,956 B1 | 7/2001 | Myers et al. |
| 6,266,162 B1 | 7/2001 | Okamura et al. |
| 6,266,577 B1 | 7/2001 | Popp et al. |
| 6,289,263 B1 | 9/2001 | Mukherjee |
| 6,292,713 B1 | 9/2001 | Jouppi et al. |
| 6,304,050 B1 | 10/2001 | Skaar et al. |
| 6,314,631 B1 * | 11/2001 | Pryor ................. 29/407.04 |
| 6,317,652 B1 | 11/2001 | Osada |
| 6,317,953 B1 * | 11/2001 | Pryor ................. 29/407.04 |
| 6,321,137 B1 | 11/2001 | De Smet |
| 6,324,184 B1 | 11/2001 | Hou et al. |
| 6,324,443 B1 | 11/2001 | Kurakake et al. |
| 6,325,756 B1 | 12/2001 | Webb et al. |
| 6,327,516 B1 | 12/2001 | Zenke |
| 6,330,486 B1 | 12/2001 | Padula |
| 6,330,493 B1 | 12/2001 | Takahashi et al. |
| 6,331,181 B1 * | 12/2001 | Tierney et al. ............ 606/130 |
| 6,346,950 B1 | 2/2002 | Jouppi |
| 6,346,962 B1 | 2/2002 | Goodridge |
| 6,369,847 B1 | 4/2002 | James et al. |
| 6,373,855 B1 | 4/2002 | Downing et al. |
| 6,381,515 B1 | 4/2002 | Inoue et al. |
| 6,389,329 B1 | 5/2002 | Colens |
| 6,400,378 B1 | 6/2002 | Snook |
| 6,408,230 B2 | 6/2002 | Wada |
| 6,430,471 B1 | 8/2002 | Kintou et al. |
| 6,430,475 B2 | 8/2002 | Okamoto et al. |
| 6,438,457 B1 | 8/2002 | Yokoo et al. |
| 6,445,964 B1 | 9/2002 | White et al. |
| 6,449,762 B1 | 9/2002 | McElvain |
| 6,452,915 B1 | 9/2002 | Jorgensen |
| 6,457,043 B1 | 9/2002 | Kwak et al. |
| 6,459,955 B1 | 10/2002 | Bartsch et al. |
| 6,463,352 B1 | 10/2002 | Tadokoro et al. |
| 6,463,361 B1 | 10/2002 | Wang et al. |
| 6,466,844 B1 | 10/2002 | Ikeda et al. |
| 6,468,265 B1 | 10/2002 | Evans et al. |
| 6,470,235 B2 | 10/2002 | Kasuga et al. |
| 6,474,434 B1 | 11/2002 | Bech |
| 6,480,762 B1 | 11/2002 | Uchikubo et al. |
| 6,491,701 B2 | 12/2002 | Tierney et al. |
| 6,496,099 B2 | 12/2002 | Wang et al. |
| 6,496,755 B2 | 12/2002 | Wallach et al. |
| 6,501,740 B1 | 12/2002 | Sun et al. |
| 6,507,773 B2 | 1/2003 | Parker et al. |
| 6,522,906 B1 | 2/2003 | Salisbury, Jr. et al. |
| 6,523,629 B1 | 2/2003 | Buttz et al. |
| 6,526,332 B2 | 2/2003 | Sakamoto et al. |
| 6,529,620 B2 | 3/2003 | Thompson |
| 6,529,765 B1 | 3/2003 | Franck et al. |
| 6,529,802 B1 | 3/2003 | Kawakita et al. |
| 6,532,404 B2 | 3/2003 | Colens |
| 6,535,182 B2 | 3/2003 | Stanton |
| 6,535,793 B2 | 3/2003 | Allard |
| 6,540,039 B1 | 4/2003 | Yu et al. |
| 6,543,899 B2 | 4/2003 | Covannon et al. |
| 6,549,215 B2 | 4/2003 | Jouppi |
| 6,563,533 B1 | 5/2003 | Colby |
| 6,567,038 B1 | 5/2003 | Granot et al. |
| 6,580,246 B2 | 6/2003 | Jacobs |
| 6,581,798 B2 | 6/2003 | Liff et al. |
| 6,584,376 B1 | 6/2003 | Van Kommer |
| 6,587,750 B2 | 7/2003 | Gerbi et al. |
| 6,590,604 B1 | 7/2003 | Tucker et al. |
| 6,594,269 B1 | 7/2003 | Polcyn |
| 6,594,552 B1 * | 7/2003 | Nowlin et al. ............ 700/260 |
| 6,597,392 B1 | 7/2003 | Jenkins et al. |
| 6,602,469 B1 | 8/2003 | Maus et al. |
| 6,604,019 B2 | 8/2003 | Ahlin et al. |
| 6,604,021 B2 | 8/2003 | Imai et al. |
| 6,611,120 B2 | 8/2003 | Song et al. |
| 6,643,496 B1 | 11/2003 | Shimoyama et al. |
| 6,646,677 B2 | 11/2003 | Noro et al. |
| 6,650,748 B1 | 11/2003 | Edwards et al. |
| 6,666,374 B1 | 12/2003 | Green et al. |
| 6,684,129 B2 | 1/2004 | Salisbury, Jr. et al. |
| 6,691,000 B2 | 2/2004 | Nagai et al. |
| 6,693,585 B1 | 2/2004 | MacLeod |
| 6,710,797 B1 | 3/2004 | McNelley et al. |
| 6,724,823 B2 | 4/2004 | Rovati et al. |
| 6,728,599 B2 | 4/2004 | Wang et al. |
| 6,763,282 B2 | 7/2004 | Glenn et al. |
| 6,764,373 B1 | 7/2004 | Osawa et al. |
| 6,769,771 B2 | 8/2004 | Trumbull |
| 6,781,606 B2 | 8/2004 | Jouppi |
| 6,784,916 B2 | 8/2004 | Smith |
| 6,785,589 B2 | 8/2004 | Eggenberger et al. |
| 6,791,550 B2 | 9/2004 | Goldhor et al. |
| 6,798,753 B1 | 9/2004 | Doganata et al. |
| 6,799,065 B1 | 9/2004 | Niemeyer |
| 6,799,088 B2 | 9/2004 | Wang et al. |
| 6,804,580 B1 | 10/2004 | Stoddard et al. |
| 6,804,656 B1 | 10/2004 | Rosenfeld et al. |
| 6,810,411 B1 | 10/2004 | Coughlin et al. |
| 6,816,192 B1 | 11/2004 | Nishikawa |
| 6,816,754 B2 | 11/2004 | Mukai et al. |
| 6,836,703 B2 | 12/2004 | Wang et al. |
| 6,839,612 B2 | 1/2005 | Sanchez et al. |
| 6,840,904 B2 | 1/2005 | Goldberg |
| 6,845,297 B2 | 1/2005 | Allard |
| 6,852,107 B2 | 2/2005 | Wang et al. |
| 6,853,878 B2 | 2/2005 | Hirayama et al. |
| 6,853,880 B2 | 2/2005 | Sakagami et al. |
| 6,871,117 B2 | 3/2005 | Wang et al. |
| 6,879,879 B2 | 4/2005 | Jouppi et al. |
| 6,888,333 B2 | 5/2005 | Laby |
| 6,892,112 B2 | 5/2005 | Wang et al. |
| 6,893,267 B1 | 5/2005 | Yueh |
| 6,895,305 B2 | 5/2005 | Lathan et al. |
| 6,898,484 B2 | 5/2005 | Lemelson et al. |
| 6,914,622 B1 | 7/2005 | Smith et al. |
| 6,925,357 B2 | 8/2005 | Wang et al. |
| 6,951,535 B2 | 10/2005 | Ghodoussi et al. |
| 6,952,470 B1 | 10/2005 | Tioe et al. |
| 6,957,712 B2 | 10/2005 | Song et al. |
| 6,958,706 B2 | 10/2005 | Chaco et al. |
| 6,965,394 B2 | 11/2005 | Gutta et al. |
| 6,990,112 B1 | 1/2006 | Brent et al. |
| 6,995,664 B1 | 2/2006 | Darling |
| 7,007,235 B1 | 2/2006 | Hussein et al. |
| 7,011,538 B2 | 3/2006 | Chang |
| 7,015,934 B2 | 3/2006 | Toyama et al. |
| RE39,080 E | 4/2006 | Johnston |
| 7,030,757 B2 | 4/2006 | Matsuhira et al. |
| 7,053,578 B2 | 5/2006 | Diehl et al. |
| 7,055,210 B2 | 6/2006 | Keppler et al. |
| 7,058,689 B2 | 6/2006 | Parker et al. |
| 7,092,001 B2 | 8/2006 | Schulz |
| 7,096,090 B1 | 8/2006 | Zweig |
| 7,115,102 B2 | 10/2006 | Abbruscato |
| 7,117,067 B2 | 10/2006 | McLurkin et al. |
| 7,123,285 B2 | 10/2006 | Smith et al. |
| 7,123,974 B1 | 10/2006 | Hamilton |
| 7,123,991 B2 | 10/2006 | Graf et al. |
| 7,127,325 B2 | 10/2006 | Nagata et al. |
| 7,129,970 B2 | 10/2006 | James et al. |
| 7,133,062 B2 | 11/2006 | Castles et al. |
| 7,142,945 B2 | 11/2006 | Wang et al. |
| 7,142,947 B2 | 11/2006 | Wang et al. |
| 7,151,982 B2 | 12/2006 | Liff et al. |
| 7,154,526 B2 | 12/2006 | Foote et al. |
| 7,155,306 B2 | 12/2006 | Haitin et al. |
| 7,156,809 B2 | 1/2007 | Quy |
| 7,158,859 B2 | 1/2007 | Wang et al. |
| 7,158,860 B2 | 1/2007 | Wang et al. |
| 7,158,861 B2 | 1/2007 | Wang et al. |
| 7,161,322 B2 | 1/2007 | Wang et al. |
| 7,162,338 B2 | 1/2007 | Goncalves et al. |
| 7,164,969 B2 | 1/2007 | Wang et al. |

(56) References Cited

U.S. PATENT DOCUMENTS

| | | | |
|---|---|---|---|
| 7,164,970 B2 | 1/2007 | Wang et al. | |
| 7,167,448 B2 | 1/2007 | Wookey et al. | |
| 7,171,286 B2 | 1/2007 | Wang et al. | |
| 7,174,238 B1 | 2/2007 | Zweig | |
| 7,181,455 B2 | 2/2007 | Wookey et al. | |
| 7,184,559 B2 | 2/2007 | Jouppi | |
| 7,188,000 B2 | 3/2007 | Chiappetta et al. | |
| 7,199,790 B2 | 4/2007 | Rosenberg et al. | |
| 7,202,851 B2 | 4/2007 | Cunningham et al. | |
| 7,206,627 B2 | 4/2007 | Abovitz et al. | |
| 7,215,786 B2 | 5/2007 | Nakadai et al. | |
| 7,219,364 B2 | 5/2007 | Bolle et al. | |
| 7,222,000 B2 * | 5/2007 | Wang et al. | 700/259 |
| 7,227,334 B2 | 6/2007 | Yang et al. | |
| 7,256,708 B2 | 8/2007 | Rosenfeld et al. | |
| 7,262,573 B2 | 8/2007 | Wang et al. | |
| 7,283,153 B2 | 10/2007 | Provost et al. | |
| 7,289,883 B2 | 10/2007 | Wang et al. | |
| 7,292,257 B2 | 11/2007 | Kang et al. | |
| 7,292,912 B2 | 11/2007 | Wang et al. | |
| 7,305,114 B2 | 12/2007 | Wolff et al. | |
| 7,317,685 B1 | 1/2008 | Flott et al. | |
| 7,321,807 B2 | 1/2008 | Laski | |
| 7,332,890 B2 | 2/2008 | Cohen et al. | |
| 7,333,642 B2 | 2/2008 | Green | |
| 7,346,429 B2 | 3/2008 | Goldenberg et al. | |
| 7,352,153 B2 | 4/2008 | Yan | |
| 7,363,121 B1 | 4/2008 | Chen et al. | |
| 7,382,399 B1 | 6/2008 | McCall et al. | |
| 7,386,730 B2 | 6/2008 | Uchikubo | |
| 7,391,432 B2 | 6/2008 | Terada | |
| 7,400,578 B2 | 7/2008 | Guthrie et al. | |
| 7,404,140 B2 | 7/2008 | O'Rourke | |
| 7,421,470 B2 | 9/2008 | Ludwig et al. | |
| 7,430,209 B2 | 9/2008 | Porter | |
| 7,432,949 B2 | 10/2008 | Remy et al. | |
| 7,433,921 B2 | 10/2008 | Ludwig et al. | |
| 7,441,953 B2 | 10/2008 | Banks | |
| 7,492,731 B2 | 2/2009 | Hagendorf | |
| 7,510,428 B2 | 3/2009 | Obata et al. | |
| 7,523,069 B1 | 4/2009 | Friedl et al. | |
| 7,525,281 B2 | 4/2009 | Koyanagi et al. | |
| 7,535,486 B2 | 5/2009 | Motomura et al. | |
| 7,557,758 B2 | 7/2009 | Rofougaran | |
| 7,587,260 B2 | 9/2009 | Bruemmer et al. | |
| 7,587,512 B2 | 9/2009 | Ta et al. | |
| 7,590,060 B2 | 9/2009 | Miceli | |
| 7,593,030 B2 | 9/2009 | Wang et al. | |
| 7,599,290 B2 | 10/2009 | Dos Remedios et al. | |
| 7,624,166 B2 | 11/2009 | Foote et al. | |
| 7,630,314 B2 | 12/2009 | Dos Remedios et al. | |
| 7,631,833 B1 * | 12/2009 | Ghaleb et al. | 244/3.15 |
| 7,643,051 B2 | 1/2010 | Sandberg et al. | |
| 7,647,320 B2 | 1/2010 | Mok et al. | |
| 7,657,560 B1 | 2/2010 | DiRienzo | |
| 7,680,038 B1 | 3/2010 | Gourlay | |
| 7,693,757 B2 | 4/2010 | Zimmerman | |
| 7,698,432 B2 | 4/2010 | Short et al. | |
| 7,703,113 B2 | 4/2010 | Dawson | |
| 7,719,229 B2 | 5/2010 | Kaneko et al. | |
| 7,737,993 B2 | 6/2010 | Kaasila et al. | |
| 7,739,383 B1 | 6/2010 | Short et al. | |
| 7,756,614 B2 | 7/2010 | Jouppi | |
| 7,761,185 B2 | 7/2010 | Wang et al. | |
| 7,769,492 B2 | 8/2010 | Wang et al. | |
| 7,769,705 B1 | 8/2010 | Luechtefeld | |
| 7,774,158 B2 | 8/2010 | Domingues Goncalves et al. | |
| 7,797,168 B2 * | 9/2010 | Kusumoto et al. | 705/1.1 |
| 7,813,836 B2 | 10/2010 | Wang et al. | |
| 7,831,575 B2 | 11/2010 | Trossell et al. | |
| 7,835,775 B2 | 11/2010 | Sawayama et al. | |
| 7,860,680 B2 | 12/2010 | Arms et al. | |
| 7,861,366 B2 | 1/2011 | Hahm et al. | |
| 7,885,822 B2 | 2/2011 | Akers et al. | |
| 7,890,382 B2 | 2/2011 | Robb et al. | |
| 7,912,583 B2 | 3/2011 | Gutmann et al. | |
| RE42,288 E | 4/2011 | Degioanni | |
| 7,924,323 B2 | 4/2011 | Walker et al. | |
| 7,949,616 B2 * | 5/2011 | Levy et al. | 706/11 |
| 7,956,894 B2 | 6/2011 | Akers et al. | |
| 7,957,837 B2 | 6/2011 | Ziegler et al. | |
| 7,982,763 B2 | 7/2011 | King | |
| 7,982,769 B2 | 7/2011 | Jenkins et al. | |
| 7,987,069 B2 | 7/2011 | Rodgers et al. | |
| 7,996,264 B2 * | 8/2011 | Kusumoto et al. | 705/14.16 |
| 8,072,481 B1 * | 12/2011 | McNelley et al. | 348/14.16 |
| 8,077,963 B2 | 12/2011 | Wang et al. | |
| 8,116,910 B2 * | 2/2012 | Walters et al. | 700/259 |
| 8,126,960 B2 | 2/2012 | Obradovich et al. | |
| 8,170,241 B2 | 5/2012 | Roe et al. | |
| 8,179,418 B2 * | 5/2012 | Wright et al. | 348/14.05 |
| 8,180,486 B2 | 5/2012 | Saito et al. | |
| 8,209,051 B2 | 6/2012 | Wang et al. | |
| 8,212,533 B2 | 7/2012 | Ota | |
| 8,265,793 B2 | 9/2012 | Cross et al. | |
| 8,287,522 B2 | 10/2012 | Moses et al. | |
| 8,292,807 B2 | 10/2012 | Perkins et al. | |
| 8,320,534 B2 | 11/2012 | Kim et al. | |
| 8,340,654 B2 | 12/2012 | Bratton et al. | |
| 8,340,819 B2 | 12/2012 | Mangaser et al. | |
| 8,348,675 B2 | 1/2013 | Dohrmann | |
| 8,374,171 B2 | 2/2013 | Cho et al. | |
| 8,400,491 B1 | 3/2013 | Panpaliya et al. | |
| 8,401,275 B2 * | 3/2013 | Wang et al. | 382/153 |
| 8,423,284 B2 | 4/2013 | O'Shea | |
| 8,451,731 B1 | 5/2013 | Lee et al. | |
| 8,463,435 B2 | 6/2013 | Herzog et al. | |
| 8,503,340 B1 | 8/2013 | Xu | |
| 8,515,577 B2 * | 8/2013 | Wang et al. | 700/247 |
| 8,527,094 B2 | 9/2013 | Kumar et al. | |
| 8,532,860 B2 | 9/2013 | Daly | |
| 8,610,786 B2 | 12/2013 | Ortiz | |
| 8,639,797 B1 | 1/2014 | Pan et al. | |
| 8,670,017 B2 * | 3/2014 | Stuart et al. | 348/14.05 |
| 8,726,454 B2 | 5/2014 | Gilbert, Jr. et al. | |
| 8,836,751 B2 * | 9/2014 | Ballantyne et al. | 348/14.05 |
| 8,849,679 B2 * | 9/2014 | Wang et al. | 705/2 |
| 8,849,680 B2 * | 9/2014 | Wright et al. | 705/2 |
| 8,861,750 B2 * | 10/2014 | Roe et al. | 381/122 |
| 8,897,920 B2 | 11/2014 | Wang et al. | |
| 8,902,278 B2 | 12/2014 | Pinter et al. | |
| 2001/0002448 A1 | 5/2001 | Wilson et al. | |
| 2001/0010053 A1 | 7/2001 | Ben-Shachar et al. | |
| 2001/0020200 A1 | 9/2001 | Das et al. | |
| 2001/0034475 A1 | 10/2001 | Flach et al. | |
| 2001/0034544 A1 | 10/2001 | Mo | |
| 2001/0037163 A1 | 11/2001 | Allard | |
| 2001/0048464 A1 | 12/2001 | Barnett | |
| 2001/0051881 A1 | 12/2001 | Filler | |
| 2001/0054071 A1 | 12/2001 | Loeb | |
| 2001/0055373 A1 | 12/2001 | Yamashita | |
| 2002/0015296 A1 | 2/2002 | Howell et al. | |
| 2002/0027597 A1 | 3/2002 | Sachau | |
| 2002/0027652 A1 | 3/2002 | Paromtchik et al. | |
| 2002/0033880 A1 | 3/2002 | Sul et al. | |
| 2002/0038168 A1 | 3/2002 | Kasuga et al. | |
| 2002/0044201 A1 | 4/2002 | Alexander et al. | |
| 2002/0049517 A1 | 4/2002 | Ruffner | |
| 2002/0055917 A1 | 5/2002 | Muraca | |
| 2002/0057279 A1 | 5/2002 | Jouppi | |
| 2002/0058929 A1 | 5/2002 | Green | |
| 2002/0059587 A1 | 5/2002 | Cofano et al. | |
| 2002/0063726 A1 | 5/2002 | Jouppi | |
| 2002/0073429 A1 | 6/2002 | Beane et al. | |
| 2002/0082498 A1 | 6/2002 | Wendt et al. | |
| 2002/0085030 A1 | 7/2002 | Ghani | |
| 2002/0095238 A1 | 7/2002 | Ahlin et al. | |
| 2002/0095239 A1 | 7/2002 | Wallach et al. | |
| 2002/0098879 A1 | 7/2002 | Rheey | |
| 2002/0104094 A1 | 8/2002 | Alexander et al. | |
| 2002/0106998 A1 | 8/2002 | Presley et al. | |
| 2002/0109770 A1 | 8/2002 | Terada | |
| 2002/0109775 A1 * | 8/2002 | White et al. | 348/87 |
| 2002/0111988 A1 | 8/2002 | Sato | |

(56) References Cited

U.S. PATENT DOCUMENTS

| | | |
|---|---|---|
| 2002/0120362 A1 | 8/2002 | Lathan et al. |
| 2002/0128985 A1* | 9/2002 | Greenwald .................. 705/400 |
| 2002/0130950 A1 | 9/2002 | James et al. |
| 2002/0133062 A1 | 9/2002 | Arling et al. |
| 2002/0141595 A1 | 10/2002 | Jouppi |
| 2002/0143923 A1 | 10/2002 | Alexander |
| 2002/0177925 A1 | 11/2002 | Onishi et al. |
| 2002/0183894 A1 | 12/2002 | Wang et al. |
| 2002/0184674 A1 | 12/2002 | Xi et al. |
| 2002/0186243 A1 | 12/2002 | Ellis et al. |
| 2003/0021107 A1 | 1/2003 | Howell et al. |
| 2003/0030397 A1 | 2/2003 | Simmons |
| 2003/0048481 A1 | 3/2003 | Kobayashi et al. |
| 2003/0050733 A1 | 3/2003 | Wang et al. |
| 2003/0050734 A1 | 3/2003 | Lapham |
| 2003/0060808 A1 | 3/2003 | Wilk |
| 2003/0063600 A1 | 4/2003 | Noma et al. |
| 2003/0069752 A1 | 4/2003 | Ledain et al. |
| 2003/0080901 A1 | 5/2003 | Piotrowski |
| 2003/0100892 A1 | 5/2003 | Morley et al. |
| 2003/0104806 A1 | 6/2003 | Ruef et al. |
| 2003/0112823 A1 | 6/2003 | Collins et al. |
| 2003/0114962 A1 | 6/2003 | Niemeyer et al. |
| 2003/0120714 A1 | 6/2003 | Wolff et al. |
| 2003/0126361 A1 | 7/2003 | Slater et al. |
| 2003/0135097 A1 | 7/2003 | Wiederhold et al. |
| 2003/0135203 A1 | 7/2003 | Wang et al. |
| 2003/0144579 A1 | 7/2003 | Buss |
| 2003/0144649 A1 | 7/2003 | Ghodoussi et al. |
| 2003/0151658 A1 | 8/2003 | Smith |
| 2003/0152145 A1 | 8/2003 | Kawakita |
| 2003/0171710 A1 | 9/2003 | Bassuk et al. |
| 2003/0174285 A1 | 9/2003 | Trumbull |
| 2003/0180697 A1 | 9/2003 | Kim et al. |
| 2003/0195662 A1 | 10/2003 | Wang et al. |
| 2003/0199000 A1 | 10/2003 | Valkirs et al. |
| 2003/0206242 A1 | 11/2003 | Choi |
| 2003/0212472 A1 | 11/2003 | McKee |
| 2003/0216833 A1 | 11/2003 | Mukai et al. |
| 2003/0216834 A1 | 11/2003 | Allard |
| 2003/0220541 A1 | 11/2003 | Salisbury, Jr. et al. |
| 2003/0220715 A1 | 11/2003 | Kneifel, II et al. |
| 2003/0231244 A1 | 12/2003 | Bonilla et al. |
| 2003/0232649 A1 | 12/2003 | Gizis et al. |
| 2003/0236590 A1 | 12/2003 | Park et al. |
| 2004/0001197 A1 | 1/2004 | Ko et al. |
| 2004/0001676 A1 | 1/2004 | Colgan et al. |
| 2004/0008138 A1 | 1/2004 | Hockley, Jr. et al. |
| 2004/0010344 A1 | 1/2004 | Hiratsuka et al. |
| 2004/0012362 A1 | 1/2004 | Tsurumi |
| 2004/0013295 A1 | 1/2004 | Sabe et al. |
| 2004/0017475 A1 | 1/2004 | Akers et al. |
| 2004/0019406 A1 | 1/2004 | Wang et al. |
| 2004/0024490 A1 | 2/2004 | McLurkin et al. |
| 2004/0041904 A1 | 3/2004 | Lapalme et al. |
| 2004/0065073 A1 | 4/2004 | Nash |
| 2004/0068657 A1 | 4/2004 | Alexander et al. |
| 2004/0078219 A1 | 4/2004 | Kaylor et al. |
| 2004/0080610 A1 | 4/2004 | James et al. |
| 2004/0088077 A1 | 5/2004 | Jouppi et al. |
| 2004/0088078 A1 | 5/2004 | Jouppi et al. |
| 2004/0093409 A1 | 5/2004 | Thompson et al. |
| 2004/0095516 A1 | 5/2004 | Rohlicek |
| 2004/0098167 A1 | 5/2004 | Yi et al. |
| 2004/0102167 A1 | 5/2004 | Shim et al. |
| 2004/0107254 A1 | 6/2004 | Ludwig et al. |
| 2004/0107255 A1 | 6/2004 | Ludwig et al. |
| 2004/0117065 A1 | 6/2004 | Wang et al. |
| 2004/0117067 A1 | 6/2004 | Jouppi |
| 2004/0123158 A1 | 6/2004 | Roskind |
| 2004/0135879 A1 | 7/2004 | Stacy et al. |
| 2004/0138547 A1 | 7/2004 | Wang et al. |
| 2004/0143421 A1 | 7/2004 | Wang et al. |
| 2004/0148638 A1 | 7/2004 | Weisman et al. |
| 2004/0150725 A1 | 8/2004 | Taguchi |
| 2004/0153211 A1 | 8/2004 | Kamoto et al. |
| 2004/0157612 A1 | 8/2004 | Kim |
| 2004/0162637 A1 | 8/2004 | Wang et al. |
| 2004/0167666 A1 | 8/2004 | Wang et al. |
| 2004/0167668 A1 | 8/2004 | Wang et al. |
| 2004/0168148 A1 | 8/2004 | Goncalves et al. |
| 2004/0170300 A1 | 9/2004 | Jouppi |
| 2004/0172301 A1 | 9/2004 | Mihai et al. |
| 2004/0172306 A1 | 9/2004 | Wohl et al. |
| 2004/0174129 A1 | 9/2004 | Wang et al. |
| 2004/0175684 A1 | 9/2004 | Kaasa et al. |
| 2004/0179714 A1 | 9/2004 | Jouppi |
| 2004/0186623 A1 | 9/2004 | Dooley et al. |
| 2004/0189700 A1 | 9/2004 | Mandavilli et al. |
| 2004/0201602 A1 | 10/2004 | Mody et al. |
| 2004/0205664 A1 | 10/2004 | Prendergast |
| 2004/0215490 A1 | 10/2004 | Duchon et al. |
| 2004/0218099 A1 | 11/2004 | Washington |
| 2004/0222638 A1 | 11/2004 | Bednyak |
| 2004/0224676 A1 | 11/2004 | Iseki |
| 2004/0230340 A1 | 11/2004 | Fukuchi et al. |
| 2004/0240981 A1 | 12/2004 | Dothan et al. |
| 2004/0241981 A1 | 12/2004 | Doris et al. |
| 2005/0003330 A1 | 1/2005 | Asgarinejad et al. |
| 2005/0004708 A1 | 1/2005 | Goldenberg et al. |
| 2005/0007445 A1 | 1/2005 | Foote et al. |
| 2005/0013149 A1 | 1/2005 | Trossell |
| 2005/0021182 A1 | 1/2005 | Wang et al. |
| 2005/0021183 A1 | 1/2005 | Wang et al. |
| 2005/0021187 A1 | 1/2005 | Wang et al. |
| 2005/0021309 A1 | 1/2005 | Alexander et al. |
| 2005/0024485 A1 | 2/2005 | Castles et al. |
| 2005/0027567 A1 | 2/2005 | Taha |
| 2005/0027794 A1 | 2/2005 | Decker |
| 2005/0028221 A1 | 2/2005 | Liu et al. |
| 2005/0035862 A1 | 2/2005 | Wildman et al. |
| 2005/0038416 A1 | 2/2005 | Wang et al. |
| 2005/0038564 A1 | 2/2005 | Burick |
| 2005/0049898 A1 | 3/2005 | Hirakawa |
| 2005/0052527 A1 | 3/2005 | Remy et al. |
| 2005/0060211 A1 | 3/2005 | Xiao et al. |
| 2005/0065435 A1 | 3/2005 | Rauch et al. |
| 2005/0065438 A1 | 3/2005 | Miller |
| 2005/0065659 A1 | 3/2005 | Tanaka et al. |
| 2005/0065813 A1 | 3/2005 | Mishelevich et al. |
| 2005/0071046 A1 | 3/2005 | Miyazaki et al. |
| 2005/0073575 A1 | 4/2005 | Thacher et al. |
| 2005/0078816 A1 | 4/2005 | Sekiguchi et al. |
| 2005/0083011 A1 | 4/2005 | Yang et al. |
| 2005/0099493 A1 | 5/2005 | Chew |
| 2005/0104964 A1 | 5/2005 | Bovyrin et al. |
| 2005/0110867 A1 | 5/2005 | Schulz |
| 2005/0122390 A1 | 6/2005 | Wang et al. |
| 2005/0125083 A1 | 6/2005 | Kiko |
| 2005/0125098 A1 | 6/2005 | Wang et al. |
| 2005/0149364 A1 | 7/2005 | Ombrellaro |
| 2005/0152447 A1 | 7/2005 | Jouppi et al. |
| 2005/0152565 A1 | 7/2005 | Jouppi et al. |
| 2005/0154265 A1 | 7/2005 | Miro et al. |
| 2005/0168568 A1 | 8/2005 | Jouppi |
| 2005/0182322 A1 | 8/2005 | Grispo |
| 2005/0192721 A1 | 9/2005 | Jouppi |
| 2005/0204438 A1 | 9/2005 | Wang et al. |
| 2005/0212478 A1 | 9/2005 | Takenaka |
| 2005/0219356 A1 | 10/2005 | Smith et al. |
| 2005/0225634 A1 | 10/2005 | Brunetti et al. |
| 2005/0231156 A1 | 10/2005 | Yan |
| 2005/0231586 A1 | 10/2005 | Rodman et al. |
| 2005/0232647 A1 | 10/2005 | Takenaka |
| 2005/0234592 A1 | 10/2005 | McGee et al. |
| 2005/0264649 A1 | 12/2005 | Chang et al. |
| 2005/0267826 A1 | 12/2005 | Levy et al. |
| 2005/0283414 A1 | 12/2005 | Fernandes et al. |
| 2005/0286759 A1 | 12/2005 | Zitnick et al. |
| 2006/0007943 A1 | 1/2006 | Fellman |
| 2006/0010028 A1 | 1/2006 | Sorensen |
| 2006/0013263 A1 | 1/2006 | Fellman |
| 2006/0013469 A1 | 1/2006 | Wang et al. |
| 2006/0013488 A1 | 1/2006 | Inoue |

(56) References Cited

U.S. PATENT DOCUMENTS

| | | |
|---|---|---|
| 2006/0014388 A1 | 1/2006 | Lur et al. |
| 2006/0020694 A1 | 1/2006 | Nag et al. |
| 2006/0029065 A1 | 2/2006 | Fellman |
| 2006/0047365 A1 | 3/2006 | Ghodoussi et al. |
| 2006/0048286 A1 | 3/2006 | Donato |
| 2006/0052676 A1 | 3/2006 | Wang et al. |
| 2006/0052684 A1 | 3/2006 | Takahashi et al. |
| 2006/0056655 A1 | 3/2006 | Wen et al. |
| 2006/0056837 A1 | 3/2006 | Vapaakoski |
| 2006/0064212 A1 | 3/2006 | Thorne |
| 2006/0066609 A1 | 3/2006 | Iodice et al. |
| 2006/0071797 A1 | 4/2006 | Rosenfeld et al. |
| 2006/0074525 A1 | 4/2006 | Close et al. |
| 2006/0074719 A1 | 4/2006 | Horner |
| 2006/0082642 A1 | 4/2006 | Wang et al. |
| 2006/0087746 A1 | 4/2006 | Lipow |
| 2006/0095158 A1 | 5/2006 | Lee et al. |
| 2006/0095170 A1 | 5/2006 | Yang et al. |
| 2006/0098573 A1 | 5/2006 | Beer et al. |
| 2006/0103659 A1 | 5/2006 | Karandikar et al. |
| 2006/0104279 A1 | 5/2006 | Fellman et al. |
| 2006/0106493 A1 | 5/2006 | Niemeyer et al. |
| 2006/0122482 A1 | 6/2006 | Mariotti et al. |
| 2006/0125356 A1 | 6/2006 | Meek, Jr. et al. |
| 2006/0142983 A1 | 6/2006 | Sorensen et al. |
| 2006/0149418 A1 | 7/2006 | Anvari |
| 2006/0161136 A1 | 7/2006 | Anderson |
| 2006/0161303 A1 | 7/2006 | Wang et al. |
| 2006/0164546 A1 | 7/2006 | Adachi |
| 2006/0171515 A1 | 8/2006 | Hintermeister et al. |
| 2006/0173708 A1 | 8/2006 | Vining et al. |
| 2006/0173712 A1 | 8/2006 | Joubert |
| 2006/0178559 A1 | 8/2006 | Kumar et al. |
| 2006/0178776 A1 | 8/2006 | Feingold et al. |
| 2006/0178777 A1 | 8/2006 | Park et al. |
| 2006/0189393 A1 | 8/2006 | Edery |
| 2006/0195569 A1 | 8/2006 | Barker |
| 2006/0224781 A1 | 10/2006 | Tsao et al. |
| 2006/0247045 A1 | 11/2006 | Jeong et al. |
| 2006/0259193 A1 | 11/2006 | Wang et al. |
| 2006/0268704 A1 | 11/2006 | Ansari et al. |
| 2006/0271238 A1 | 11/2006 | Choi et al. |
| 2006/0271400 A1 | 11/2006 | Clements et al. |
| 2006/0293788 A1 | 12/2006 | Pogodin |
| 2007/0021871 A1 | 1/2007 | Wang et al. |
| 2007/0025711 A1 | 2/2007 | Marcus |
| 2007/0046237 A1 | 3/2007 | Lakshmanan et al. |
| 2007/0050937 A1 | 3/2007 | Song et al. |
| 2007/0064092 A1 | 3/2007 | Sandbeg et al. |
| 2007/0078566 A1 | 4/2007 | Wang et al. |
| 2007/0093279 A1 | 4/2007 | Janik |
| 2007/0112700 A1 | 5/2007 | Den Haan et al. |
| 2007/0116152 A1 | 5/2007 | Thesling |
| 2007/0117516 A1 | 5/2007 | Saidi et al. |
| 2007/0120965 A1 | 5/2007 | Sandberg et al. |
| 2007/0122783 A1 | 5/2007 | Habashi |
| 2007/0133407 A1 | 6/2007 | Choi et al. |
| 2007/0135967 A1 | 6/2007 | Jung et al. |
| 2007/0142964 A1 | 6/2007 | Abramson |
| 2007/0170886 A1 | 7/2007 | Plishner |
| 2007/0176060 A1 | 8/2007 | White et al. |
| 2007/0192910 A1 | 8/2007 | Vu et al. |
| 2007/0197896 A1 | 8/2007 | Moll et al. |
| 2007/0198128 A1 | 8/2007 | Ziegler et al. |
| 2007/0198130 A1 | 8/2007 | Wang et al. |
| 2007/0199108 A1 | 8/2007 | Angle et al. |
| 2007/0216347 A1 | 9/2007 | Kaneko et al. |
| 2007/0226949 A1 | 10/2007 | Hahm et al. |
| 2007/0250212 A1 | 10/2007 | Halloran et al. |
| 2007/0255706 A1 | 11/2007 | Iketani et al. |
| 2007/0262884 A1 | 11/2007 | Goncalves et al. |
| 2007/0273751 A1 | 11/2007 | Sachau |
| 2007/0290040 A1 | 12/2007 | Wurman et al. |
| 2007/0291109 A1 | 12/2007 | Wang et al. |
| 2007/0291128 A1 | 12/2007 | Wang et al. |
| 2008/0009969 A1 | 1/2008 | Bruemmer et al. |
| 2008/0011904 A1 | 1/2008 | Cepollina et al. |
| 2008/0027591 A1 | 1/2008 | Lenser et al. |
| 2008/0033641 A1 | 2/2008 | Medalia |
| 2008/0045804 A1 | 2/2008 | Williams |
| 2008/0051985 A1 | 2/2008 | D'Andrea et al. |
| 2008/0065268 A1 | 3/2008 | Wang et al. |
| 2008/0082211 A1 | 4/2008 | Wang et al. |
| 2008/0086241 A1 | 4/2008 | Phillips et al. |
| 2008/0091340 A1 | 4/2008 | Milstein et al. |
| 2008/0126132 A1 | 5/2008 | Warner et al. |
| 2008/0133052 A1 | 6/2008 | Jones et al. |
| 2008/0161969 A1 | 7/2008 | Lee et al. |
| 2008/0174570 A1 | 7/2008 | Jobs et al. |
| 2008/0201016 A1 | 8/2008 | Finlay |
| 2008/0201017 A1 | 8/2008 | Wang et al. |
| 2008/0215987 A1 | 9/2008 | Alexander et al. |
| 2008/0229531 A1 | 9/2008 | Takida |
| 2008/0232763 A1 | 9/2008 | Brady |
| 2008/0255703 A1 | 10/2008 | Wang et al. |
| 2008/0263451 A1 | 10/2008 | Portele et al. |
| 2008/0267069 A1 | 10/2008 | Thielman et al. |
| 2008/0269949 A1 | 10/2008 | Norman et al. |
| 2008/0281467 A1 | 11/2008 | Pinter |
| 2008/0306375 A1 | 12/2008 | Sayler et al. |
| 2009/0030552 A1 | 1/2009 | Nakadai et al. |
| 2009/0044334 A1 | 2/2009 | Parsell et al. |
| 2009/0049640 A1 | 2/2009 | Lee et al. |
| 2009/0055023 A1 | 2/2009 | Walters et al. |
| 2009/0070135 A1 | 3/2009 | Parida et al. |
| 2009/0086013 A1 | 4/2009 | Thapa |
| 2009/0102919 A1* | 4/2009 | Zamierowski et al. ........ 348/143 |
| 2009/0105882 A1 | 4/2009 | Wang et al. |
| 2009/0106679 A1 | 4/2009 | Anzures et al. |
| 2009/0122699 A1 | 5/2009 | Alperovitch et al. |
| 2009/0125147 A1 | 5/2009 | Wang et al. |
| 2009/0144425 A1 | 6/2009 | Marr et al. |
| 2009/0164255 A1 | 6/2009 | Menschik et al. |
| 2009/0164657 A1 | 6/2009 | Li et al. |
| 2009/0171170 A1 | 7/2009 | Li et al. |
| 2009/0177323 A1 | 7/2009 | Ziegler et al. |
| 2009/0177641 A1 | 7/2009 | Raghavan |
| 2009/0237317 A1 | 9/2009 | Rofougaran |
| 2009/0240371 A1 | 9/2009 | Wang et al. |
| 2009/0248200 A1 | 10/2009 | Root |
| 2009/0259339 A1 | 10/2009 | Wright et al. |
| 2010/0010672 A1 | 1/2010 | Wang et al. |
| 2010/0010673 A1 | 1/2010 | Wang et al. |
| 2010/0017046 A1 | 1/2010 | Cheung et al. |
| 2010/0019715 A1 | 1/2010 | Roe et al. |
| 2010/0026239 A1 | 2/2010 | Li et al. |
| 2010/0030578 A1 | 2/2010 | Siddique et al. |
| 2010/0051596 A1 | 3/2010 | Diedrick et al. |
| 2010/0063848 A1 | 3/2010 | Kremer et al. |
| 2010/0066804 A1 | 3/2010 | Shoemake et al. |
| 2010/0070079 A1 | 3/2010 | Mangaser et al. |
| 2010/0073490 A1 | 3/2010 | Wang et al. |
| 2010/0076600 A1 | 3/2010 | Cross et al. |
| 2010/0085874 A1 | 4/2010 | Noy et al. |
| 2010/0088232 A1 | 4/2010 | Gale |
| 2010/0115418 A1 | 5/2010 | Wang et al. |
| 2010/0116566 A1 | 5/2010 | Ohm et al. |
| 2010/0131103 A1 | 5/2010 | Herzog et al. |
| 2010/0145479 A1 | 6/2010 | Griffiths |
| 2010/0157825 A1 | 6/2010 | Anderlind et al. |
| 2010/0171826 A1* | 7/2010 | Hamilton et al. ............. 348/135 |
| 2010/0191375 A1 | 7/2010 | Wright et al. |
| 2010/0228249 A1 | 9/2010 | Mohr et al. |
| 2010/0268383 A1 | 10/2010 | Wang et al. |
| 2010/0278086 A1 | 11/2010 | Pochiraju et al. |
| 2010/0286905 A1 | 11/2010 | Goncalves et al. |
| 2010/0301679 A1 | 12/2010 | Murray et al. |
| 2010/0323783 A1 | 12/2010 | Nonaka et al. |
| 2011/0022705 A1 | 1/2011 | Yellamraju et al. |
| 2011/0050841 A1 | 3/2011 | Wang et al. |
| 2011/0071675 A1* | 3/2011 | Wells et al. .................. 700/250 |
| 2011/0071702 A1 | 3/2011 | Wang et al. |
| 2011/0072114 A1 | 3/2011 | Hoffert et al. |
| 2011/0118748 A1* | 5/2011 | Itkowitz ........................ 606/130 |

(56) References Cited

U.S. PATENT DOCUMENTS

| | | | |
|---|---|---|---|
| 2011/0153198 A1 | 6/2011 | Kokkas et al. |
| 2011/0172822 A1 | 7/2011 | Ziegler et al. |
| 2011/0187875 A1 | 8/2011 | Sanchez et al. |
| 2011/0190930 A1 | 8/2011 | Hanrahan et al. |
| 2011/0193949 A1 | 8/2011 | Nambakam et al. |
| 2011/0195701 A1 | 8/2011 | Cook et al. |
| 2011/0213210 A1 | 9/2011 | Temby et al. |
| 2011/0218674 A1* | 9/2011 | Stuart et al. ............ 700/259 |
| 2011/0245973 A1 | 10/2011 | Wang et al. |
| 2011/0280551 A1 | 11/2011 | Sammon |
| 2011/0292193 A1 | 12/2011 | Wang et al. |
| 2011/0301759 A1 | 12/2011 | Wang et al. |
| 2011/0306400 A1 | 12/2011 | Nguyen |
| 2012/0023506 A1 | 1/2012 | Maeckel et al. |
| 2012/0036484 A1 | 2/2012 | Zhang et al. |
| 2012/0059946 A1 | 3/2012 | Wang |
| 2012/0072023 A1 | 3/2012 | Ota |
| 2012/0072024 A1 | 3/2012 | Wang et al. |
| 2012/0092157 A1 | 4/2012 | Tran |
| 2012/0095352 A1 | 4/2012 | Tran |
| 2012/0113856 A1 | 5/2012 | Krishnaswamy |
| 2012/0191246 A1 | 7/2012 | Roe et al. |
| 2012/0191464 A1 | 7/2012 | Stuart et al. |
| 2012/0203731 A1 | 8/2012 | Nelson et al. |
| 2012/0291809 A1 | 11/2012 | Kuhe et al. |
| 2013/0250938 A1 | 9/2013 | Anandakumar et al. |
| 2014/0047022 A1 | 2/2014 | Chan et al. |
| 2014/0085543 A1 | 3/2014 | Hartley et al. |
| 2014/0135990 A1* | 5/2014 | Stuart et al. ............ 700/259 |
| 2014/0139616 A1 | 5/2014 | Pinter et al. |
| 2014/0155755 A1 | 6/2014 | Pinter et al. |

FOREIGN PATENT DOCUMENTS

| | | | |
|---|---|---|---|
| CN | 1404695 A | 3/2003 |
| CN | 1554193 A | 12/2004 |
| CN | 1554985 A | 12/2004 |
| CN | 1561923 A | 1/2005 |
| CN | 1743144 A | 3/2006 |
| CN | 101049017 A | 10/2007 |
| CN | 101106939 A | 1/2008 |
| CN | 101151614 A | 3/2008 |
| CN | 100407729 C | 7/2008 |
| CN | 101390098 A | 3/2009 |
| CN | 101507260 A | 8/2009 |
| CN | 101730894 A | 6/2010 |
| CN | 101866396 A | 10/2010 |
| CN | 101978365 A | 2/2011 |
| CN | 102203759 A | 9/2011 |
| CN | 101106939 B | 11/2011 |
| EP | 466492 A2 | 1/1992 |
| EP | 488673 A2 | 6/1992 |
| EP | 981905 B1 | 1/2002 |
| EP | 1262142 A2 | 12/2002 |
| EP | 1304872 A1 | 4/2003 |
| EP | 1536660 A2 | 6/2005 |
| EP | 1573406 A2 | 9/2005 |
| EP | 1594660 A2 | 11/2005 |
| EP | 1763243 A2 | 3/2007 |
| EP | 1791464 A2 | 6/2007 |
| EP | 1800476 A2 | 6/2007 |
| EP | 1819108 A2 | 8/2007 |
| EP | 1856644 A2 | 11/2007 |
| EP | 1536660 A3 | 4/2008 |
| EP | 1928310 A2 | 6/2008 |
| EP | 1232610 B1 | 1/2009 |
| EP | 2027716 A2 | 2/2009 |
| EP | 2145274 A1 | 1/2010 |
| EP | 2214111 A2 | 8/2010 |
| EP | 2263158 A2 | 12/2010 |
| EP | 2300930 A1 | 3/2011 |
| EP | 2342651 A1 | 7/2011 |
| GB | 2431261 A | 4/2007 |
| JP | 07-194609 A | 8/1995 |
| JP | 7-213753 A | 8/1995 |
| JP | 7-248823 A | 9/1995 |
| JP | 7-257422 A | 10/1995 |
| JP | 8-84328 A | 3/1996 |
| JP | 8-320727 A | 12/1996 |
| JP | 9-267276 A | 10/1997 |
| JP | 10-79097 A | 3/1998 |
| JP | 10-288689 A | 10/1998 |
| JP | 11-220706 A | 8/1999 |
| JP | 11220706 A | 8/1999 |
| JP | 2000-32319 A | 1/2000 |
| JP | 2000-49800 A | 2/2000 |
| JP | 2000-79587 A | 3/2000 |
| JP | 2000-196876 A | 7/2000 |
| JP | 2001-125641 A | 5/2001 |
| JP | 2001-147718 A | 5/2001 |
| JP | 2001-179663 A | 7/2001 |
| JP | 2001-188124 A | 7/2001 |
| JP | 2001-198865 A | 7/2001 |
| JP | 2001-198868 A | 7/2001 |
| JP | 2001-199356 A | 7/2001 |
| JP | 2002-574 A | 1/2002 |
| JP | 2002-46088 A | 2/2002 |
| JP | 2002-101333 A | 4/2002 |
| JP | 2002-112970 A | 4/2002 |
| JP | 2002-235423 A | 8/2002 |
| JP | 2002-305743 A | 10/2002 |
| JP | 2002-321180 A | 11/2002 |
| JP | 2002-355779 A | 12/2002 |
| JP | 2004-181229 A | 7/2004 |
| JP | 2004-524824 T | 8/2004 |
| JP | 2004-261941 A | 9/2004 |
| JP | 2004-289379 A | 10/2004 |
| JP | 2005-28066 A | 2/2005 |
| JP | 2005-59170 A | 3/2005 |
| JP | 2005-111083 A | 4/2005 |
| JP | 2006-508806 A | 3/2006 |
| JP | 2006-109094 A | 4/2006 |
| JP | 2006-224294 A | 8/2006 |
| JP | 2006-246438 A | 9/2006 |
| JP | 2007-7040 A | 1/2007 |
| JP | 2007-81646 A | 3/2007 |
| JP | 2007-232208 A | 9/2007 |
| JP | 2007-316966 A | 12/2007 |
| JP | 2009-125133 A | 6/2009 |
| JP | 2010-64154 A | 3/2010 |
| JP | 2010-532109 A | 9/2010 |
| JP | 2010-246954 A | 11/2010 |
| KR | 10-2006-0037979 A | 5/2006 |
| KR | 10-2009-0012542 A | 2/2009 |
| KR | 10-2010-0019479 A | 2/2010 |
| KR | 10-2010-0139037 A | 12/2010 |
| WO | 93/06690 A1 | 4/1993 |
| WO | 97/42761 A1 | 11/1997 |
| WO | 98/51078 A1 | 11/1998 |
| WO | 99/67067 A1 | 12/1999 |
| WO | 00/25516 A1 | 5/2000 |
| WO | 00/33726 A1 | 6/2000 |
| WO | 01/31861 A1 | 5/2001 |
| WO | 03/077745 A1 | 9/2003 |
| WO | 2004/008738 A1 | 1/2004 |
| WO | 2004/012018 A2 | 2/2004 |
| WO | 2004/075456 A2 | 9/2004 |
| WO | 2006/012797 A1 | 2/2006 |
| WO | 2006/044847 A2 | 4/2006 |
| WO | 2006/078611 A2 | 7/2006 |
| WO | 2007041295 A2 | 4/2007 |
| WO | 2007/041038 A3 | 6/2007 |
| WO | 2008/100272 A2 | 8/2008 |
| WO | 2008/100272 A3 | 10/2008 |
| WO | 2009/117274 A2 | 9/2009 |
| WO | 2009/128997 A1 | 10/2009 |
| WO | 2009/145958 A2 | 12/2009 |
| WO | 2010/006205 A1 | 1/2010 |
| WO | 2010/006211 A1 | 1/2010 |
| WO | 2010/033666 A1 | 3/2010 |
| WO | 2010/047881 A1 | 4/2010 |
| WO | 2010/062798 A1 | 6/2010 |
| WO | 2010/065257 A1 | 6/2010 |

(56) References Cited

FOREIGN PATENT DOCUMENTS

| | | |
|---|---|---|
| WO | 2010/120407 A1 | 10/2010 |
| WO | 2011/028589 A2 | 3/2011 |
| WO | 2011/028589 A3 | 4/2011 |
| WO | 2011/097130 A2 | 8/2011 |
| WO | 2011/097132 A2 | 8/2011 |
| WO | 2011/109336 A2 | 9/2011 |
| WO | 2011/097132 A3 | 12/2011 |
| WO | 2011/149902 A2 | 12/2011 |

OTHER PUBLICATIONS

Ojha, Anand K., "An application of Virtual Reality in Rehabilitation", Proceedings of the 1994 IEEE Southeastcon Creative Technology Transfer, A Global Affair, Apr. 1994, pp. 4-6.

Paulos et al., "A World Wide Web Telerobotic Remote Environment Browser", available online at <http://www.w3.org/Conferences/WWW4/Papers/326/>, retrieved on Nov. 23, 2010, 1995, 15 pages.

Paulos et al., "Designing Personal Tele-Embodiment", Proceedings of IEEE International Conference on Robotics and Automation, vol. 4, May 16-20, 1998, pp. 3173-3178.

Paulos et al., "PRoP: Personal Roving Presence", ACM:CHI Proceedings of CHI, 1998, 8 pages.

Paulos et al., "Ubiquitous Tele-Embodiment: Applications and Implications", International Journal of Human Computer Studies, vol. 46, No. 6, Jun. 1997, pp. 861-877.

Paulos et al., "Video of PRoP 2 at Richmond Field Station", www.prop.org, Printout of Home Page of Website and Two-page Transcript of the Audio Portion of said PRoP Video, May 2001, 2 pages.

Paulos, Eric J., "Personal Tele-Embodiment", Dissertation, Doctor of Philosophy in Computer Science in the Graduate Division of the University of California at Berkeley, 2001, 282 pages.

Picturetel Corporation, "Introducing PictureTel Live200 for Windows NT", 1997, 63 pages.

Pin et al., "A New Family of Omnidirectional and Holonomic Wheeled Platforms for Mobile Robots", IEEE Transactions on Robotics and Automation, vol. 10, No. 4, Aug. 1994, pp. 480-489.

Piquepaille, Roland, "How New Technologies are Modifying Our Way of Life", Roland Piquepaille's Technology Trends, This Blog and its RSS Feed Are Moving, Oct. 31, 2004, 2 pages.

Radvision, "Making Sense of Bandwidth the NetSense Way", Network Congestion in Unmanaged Networks Bandwidth Estimation and Adaptation Techniques, Radvision's Netsense Technology, 2010, 7 pages.

Roach, Adam, "Automatic Call Back Service in SIP", Internet Engineering Task Force, Internet Draft, Category: Informational, Mar. 2000, 8 pages.

Rovetta et al., "A New Telerobotic Application: Remote Laparoscopic Surgery Using Satellites and Optical Fiber Networks for Data Exchange", International Journal of Robotics Research, vol. 15, No. 3, Jun. 1, 1996, pp. 267-279.

Roy et al., "Towards Personal Service Robots for the Elderly", Workshop on Interactive Robots and Entertainment (WIRE 2000), vol. 25, Apr. 30-May 1, 2000, 7 pages.

Salemi et al., "MILO: Personal Robot Platform", IEEE/RSJ International Conference on Intelligent Robots and Systems, Aug. 2005, pp. 4089-4094.

Sandt et al., "Perceptions for a Transport Robot in Public Environments", Proceedings of the IEEE/RSJ International Conference on Intelligent Robots and Systems, vol. 1, Sep. 7-11, 1997, pp. 360-365.

Sawyer, Robert J., "Inventing the Future: 2000 Years of Discovery", Available online at <http://www.sfwriter.com/pritf.htm>, retrived on May 25, 2008, Jan. 2, 2000, 2 pages.

Schaeffer et al., "Care-O-Bot™: The Concept of a System for Assisting Elderly or Disabled Persons in Home Environments", Proceedings of the 24th Annual Conference of the IEEE Industrial Electronics Society, vol. 4, 1998, pp. 2476-2481.

Schultz et al., "Web Interfaces for Mobile Robots in Public Places", IEEE Robotics and Automation Magazine, vol. 7, No. 1, Mar. 2000, pp. 48-56.

Shimoga et al., "Touch and Force Reflection for Telepresence Surgery", Proceedings of the 16th Annual International Conference of the IEEE Engineering in Medicine and Biology Society, Nov. 1994, pp. 1049-1050.

Siegwart et al., "Interacting Mobile Robots on the Web", Proceedings of the IEEE International Conference on Robotics and Automation, May 1999, pp. 10-15.

Simmons et al., "Xavier: An Autonomous Mobile Robot on the Web", IEEE Robotics and Automation Magazine, 1999, pp. 43-48.

Stephenson, Gary, "Dr. Robot Tested at Hopkins", Johns Hopkins Medical institutions, available online at <http://www.hopkinsmedicine.org/press/2003/august/030805.htm>, Aug. 5, 2003, 2 pages.

Stoianovici et al., "Robotic Tools for Minimally Invasive Urologic Surgery", Complications of Urologic Laparoscopic Surgery: Recognition, Management and Prevention, Dec. 2002, 17 pages.

Suplee, Carl, "Mastering the Robot", available online at <http://www.cs.cmu.edu-nursebotlweb/press/wash/index.html>, retrieved on Nov. 23, 2010, Sep. 17, 2000, 5 pages.

Tahboub et al., "Dynamics Analysis and Control of a Holonomic Vehicle With Continously Variable Transmission", Journal of Dynamic Systems, Measurement and Control ASME, vol. 124, Mar. 2002, pp. 118-126.

Telepresence Research, Inc., "Telepresence Mobile Robot System", available online at <http://www.telepresence.com/telepresence-research/TELEROBOT/>, retrieved on Nov. 23, 2010, Feb. 20, 1995, 3 pages.

Tendick et al., "Human-Machine Interfaces for Minimally Invasive Surgery", Proceedings of the 19th Annual International Conference of the IEEE Engineering in Medicine and Biology Society, vol. 6, Oct. 30-Nov. 2, 1997, pp. 2771-2776.

Theodosiou et al., "MuLVAT: A Video Annotation Tool Based on XML-Dictionaries and Shot Clustering", 19th International Conference, Artificial Neural Networks-ICANN, Sep. 14-17, 2009, pp. 913-922.

Thrun et al., "Probabilistic Algorithms and the Interactive Museum Tour-Guide Robot Minerva", Journal of Robotics Research, vol. 19, 2000, pp. 1-35.

Time, Lists, "Office Coworker Robot", Best Inventions of 2001, Available online at <http://content.time.com/time/specials/packages/article/0,28804,1936165_1936255_1936640,00.html>, Nov. 19, 2001, 2 pages.

Tyrrell et al., "Teleconsultation in Psychology: The Use of Videolinks for Interviewing and Assessing Elderly Patients", British Geriatrics Society, Age and Ageing, vol. 30, No. 3, May 2001, pp. 191-195.

Tzafestas et al., "VR-based Teleoperation of a Mobile Robotic Assistant: Progress Report", Technical Report DEMO 2000/13, Institute of Informatics and Telecommunications, National Center for Scientific Research "Demokritos", Athens, Greece, Nov. 2000, pp. 1-23.

Urquhart, Kim, "InTouch's Robotic Companion 'Beams Up' Healthcare Experts", Medical Device Daily, The Daily Medical Technology Newspaper, vol. 7, No. 39, Feb. 27, 2003, pp. 1-4.

Weaver et al., "Monitoring and Controling Using the Internet and Java", Proceedings of the 25th Annual Conference of the IEEE Industrial Electronics Society, vol. 3, 1999, pp. 1152-1158.

Weiss et al., "Telework and Video-Mediated Communication: Importance of Real-Time, Interactive Communication for Workers with Disabilities", Available online at <http://www.telbotics.com/research_3.htm>, retrieved on Nov. 23, 2010, 1999, 3 pages.

Weiss, et al., "PEBBLES: A Personal Technology for Meeting Education, Social and Emotional Needs of Hospitalised Children", Personal and Ubiquitous Computing, vol. 5, No. 3, Aug. 2001, pp. 157-168.

West et al., "Design of Ball Wheel Mechanisms for Omnidirectional Vehicles with Full Mobility and Invariant Kinematics", Journal of Mechanical Design, ASME, vol. 119, Jun. 1997, pp. 153-161.

Yamasaki et al., "Applying Personal Robots and Active Interface to Video Conference Systems", 6th International Conference on Human Computer Interaction, vol. B, 1995, pp. 243-248.

Yamauchi, Brian, "PackBot: A Versatile Platform for Military Robotics", Proceedings of SPIE for Military Robotics, 2004, pp. 228-237.

(56) References Cited

OTHER PUBLICATIONS

Yong et al., "Robot Task Execution with Telepresence Using Virtual Reality Technology", International Conference on Mechatronic Technology, Nov. 30-Dec. 2,1998, pp. 1-8.
Zambroski, James, "CMU, Pitt Developing 'Nursebot'", available online at <http://www.cs.cmu.edu/~nursebot/web/press/tribunereview.html>, retrieved on Jun. 26, 2012, Oct. 27, 2000, 3 pages.
Zamrazil, Kristie, "Telemedicine in Texas: Public Policy Concerns", Focus Report, House Research Organization, Texas House of Representatives, No. 76-22, May 5, 2000, pp. 1-16.
Zipperer, Lorri, "Robotic Dispensing System", ISMP Medication Safety Alert, vol. 4, No. 17, Aug. 25, 1999, pp. 1-2.
Zorn, Benjamin G., "Ubiquitous Telepresence", Department of Computer Science, University of Colorado, Mar. 18, 1996, 13 pages.
"Defendant VGo Communications, Inc.'s Invalidity Contentions Pursuant to the Feb. 27, 2012 Civil Minute Order", U.S. District Court for the Central District of California, in Case No. CV11-9185 PA, May 2, 2012, 143 pages.
"Magne Charge", Smart Power for Electric Vehicles, General Motors Corporation, Serial No. 75189637, Registration No. 2114006, Filing Date: Oct. 29,1996, Aug. 26, 1997, 2 pages.
"More Online Robots: Robots that Manipulate", available online at <http://ford.ieor.berkeley.edu/ir/robots_a2.html>, retrieved on Nov. 23, 2010, Aug. 2001, 2 pages.
"PictureTel Adds New Features and Functionality to its Award-Winning Live200 Desktop Videoconferencing System", PR Newswire Association, LLC, Gale, Cengage Learning, Jun. 13, 1997, 4 pages.
"Appeal from the U.S. District Court for the Central District of California in No. 11-CV-9185, Judge Percy Anderson", May 9, 2014, pp. 1-48.
"Google translation of: Innovations Report", From research project to television star: Care-O-bot in ZDF series, available online at <http://www.innovations-report.de/specials/printa.php?id=5157>, Sep. 28, 2001.
"MPEG File Format Summary", downloaded from: <http://www.fileformat.info/format/mpeg/egff.htm>, Feb. 1, 2001, 8 pages.
"MPEG-4: a Powerful Standard for Use in Web and Television Environments", by Rob Koenen (KPN Research), downloaded from <http://www.w3.org/Architecture/1998/06/Workshop/paper26>, Jul. 1, 1998, 4 pages.
CMU Course 16X62, "Robot user's manual", (describing the Nomad Scout), Carnegie Mellon University, Feb. 1, 2001, 11 pages.
Panusopone et al., "Performance comparison of MPEG-4 and H.263+ for streaming video pplications", Circuits Systems Signal Processing, vol. 20, No. 3, 2001, pp. 293-309.
Schraft et al., "Care-0-botTM: The Concept of a System for Assisting Elderly or Disabled Persons in Home Environments", IEEE Proceedings of the 24th Annual Conference of the Industrial Electronics Society, IECON '98, Aug. 31-Sep. 4, 1998, pp. 2476-2481.
Nomadic Technologies, Inc., "Nomad Scout User's Manual", Software Version 2.7, Part No. DOC00004, Jul. 12, 1999, pp. 1-59.
ACM Digital Library Record, Autonomous Robots, vol. 11, No. 1, Table of Content, available at <http://dl.acm.org/citation.cfm?id=591550&picked=prox&cfid=360891374&cftoken=35225929>, Jul. 2001, 2 pages.
Brenner, Pablo, "A Technical Tutorial on the IEEE 802.11 Protocol", BreezeCOM Wireless Communications, Jul. 18, 1996, pp. 1-24.
Library of Congress, "008-Fixed-Length Data Elements (NR)", MARC 21 Format for Classification Data, available at <http://www.loc.gov/marc/classification/cd008.html>, retrieved on Jul. 22, 2014, pp. 1-14.
Paulos et al., "Personal Tele-Embodiment", Chapter 9 in Goldberg et al., Ed., "Beyond Webcams", MIT Press, Jan. 4, 2002, pp. 155-167.
Paulos et al., "Social Tele-Embodiment: Understanding Presence", Autonomous Robots, vol. 11, No. 1, Kluwer Academic Publishers, Jul. 2001, pp. 87-95.
Paulos, Eric John, "Personal Tele-Embodiment", Introductory and Cover Pages from 2001 Dissertation Including Contents table, together with E-mails Relating thereto from UC Berkeley Libraries, as Shelved at UC Berkeley Engineering Library (Northern Regional Library Facility), May 8, 2002, 25 pages (including 4 pages of e-mails).
Paulos, Eric John, "Personal Tele-Embodiment", OskiCat Catalog Record, UCB Library Catalog, Results page and MARC Display, retrieved on Jun. 14, 2014, 3 pages.
Harmo et al., "Moving Eye—Interactive Telepresence over Internet with a Ball Shaped Mobile Robot", Automation Technology Laboratory, Helsinki University of Technology, 2000, 6 pages.
Haule et al., "Control Scheme for Delayed Teleoperation Tasks", Communications, Computers and Signal Processing, Proceedings of IEEE Pacific Rim Conference, May 17-19, 1995, pp. 157-160.
Hees, William P., "Communications Design for a Remote Presence Robot", CSCI E-131B, Final Project, Jan. 14, 2002, 12 pages
Herias et al., "Flexible Virtual and Remote Laboratory for Teaching Robotics", FORMATEX 2006, Proceedings of Advance in Control Education Madrid, Spain, Jun. 2006, pp. 1959-1963.
Holmberg et al., "Development of a Holonomic Mobile Robot for Mobile Manipulation Tasks", FSR'99 International Conference on Field and Service Robotics, Pittsburgh, PA, Aug. 1999, 6 pages.
Ishiguro et al., "Integrating a Perceptual Information Infrastructure with Robotic Avatars: A Framework for Tele-Existence", Intelligent Robots and Systems, Proceedings of 1999 IEEE/RSJ International Conference, vol. 2, 1999, pp. 1032-1038.
Ishihara et al., "Intelligent Microrobot DDS (Drug Delivery System) Measured and Controlled by Ultrasonics", Proceedings of IEEE/RSJ International Workshop on Intelligent Robots and Systems, vol. 2, Nov. 3-5, 1991, pp. 1145-1150.
ITU, "Call Completion Supplementary Services for H.323", ITU-T, Telecommunication Standardization Sector of ITU, H.450.9, Series H: Audiovisual and Multimedia Systems, Nov. 2000, 63 pages.
ITU, "Call Intrusion Supplementary Service for H.323", ITU-T, Telecommunication Standardization Sector of ITU, H.450.11, Series H: Audiovisual and Multimedia Systems, Mar. 2001, 59 pages.
ITU, "Packet-Based Multimedia Communications Systems", ITU-T, Telecommunication Standardization Sector of ITU, H.323, Series H: Audiovisual and Multimedia Systems, Feb. 1998, 128 pages.
ITU, "A Far End Camera Control Protocol for Videoconferences Using H.224", Transmission of Non-Telephone Signals, ITU-T, Telecommunication Standardization Sector of ITU, H.281, Nov. 1994, 12 pages.
Ivanova, Natali, "Internet Based Interface for Control of a Mobile Robot", First Degree Programme in Mathematics and Computer Science, Master•s thesis, Department of Numerical Analysis and Computer Science, 2003, 59 pages.
Jacobs et al., "Applying Telemedicine to Outpatient Physical Therapy", AMIA, Annual Symposium Proceedings, 2002, 1 page.
Jenkins et al., "Telehealth Advancing Nursing Practice", Nursing Outlook, vol. 49, No. 2, Mar. 2001, pp. 100-105.
Johanson, Mathias, "Supporting Video-Mediated Communication over the Internet", Thesis for the degree of Doctor of Philosophy, Department of Computer Engineering, Chalmers University of Technology, Gothenburg, Sweden, 2003, 222 pages.
Jouppi et al., "BiReality: Mutually-Immersive Telepresence", Multimedia '04, Proceedings of the 12th Annual ACM International Conference on Multimedia, Oct. 10-16, 2004, pp. 860-867.
Jouppi et al., "First Steps Towards Mutually-Immersive Mobile Telepresence", CSCW '02, Proceedings of the ACM conference on Computer Supported Cooperative Work, Nov. 16-20, 2002, pp. 354-363.
Kanehiro et al., "Virtual Humanoid Robot Platform to Develop Controllers of Real Humanoid Robots without Porting", Proceedings of IEEE/RSJ International Conference on Intelligent Robots and Systems, vol. 2, Oct. 29-Nov. 3, 2001, pp. 1093-1099.
Kaplan et al., "An Internet Accessible Telepresence", Multimedia Systems Journal, vol. 5, 1996, 7 pages.
Keller et al., "An Interface for Raven", The National Aviary's Teleconferencing Robot, Interaction and Visual Interface Design, School of Design, Carnegie Mellon University, 2001, 8 pages.
Khatib et al., "Robots in Human Environments", Robotics Laboratory, Department of Computer Science, Stanford University, 1999, 15 pages.

(56) References Cited

OTHER PUBLICATIONS

Knight et al., "Active Visual Alignment of a Mobile Stereo Camera Platform", Robotics and Automation, Proceedings of ICRA '00, IEEE International Conference, vol. 4, Apr. 24-28, 2000, pp. 3203-3208.

Kurlowicz et al., "The Mini Mental State Examination (MMSE)", The Hartford Institute for Geriatric Nursing, Journal of Psychiatric Research, No. 3, Jan. 1999, 2 pages.

Kuzuoka et al., "Can the GestureCam be a Surrogate?", Proceedings of the Fourth European Conference on Computer-Supported Cooperative Work, Sep. 10-14, 1995, pp. 181-196.

Lane, Earl, "Automated Aides", available online at <http://www.cs.cum.edu/nursebot/web/press/nd4380.htm>, Reterieved on Nov. 23, 2010, Oct. 17, 2000, 4 pages.

Lee et al., "A Novel Method of Surgical Instruction: International Telementoring", World Journal of Urology, vol. 16, No. 6, Dec. 1998, pp. 367-370.

Lemaire, Edward, "Using Communication Technology to Enhance Rehabilitation Services", Terry Fox Mobile Clinic, The Rehabilitation Centre, Ottawa, Canada, Version 2.0, 1998-2001, 104 pages.

Lim et al., "Control to Realize Human-Like Walking of a Biped Humanoid Robot", Systems, Man and Cybernetics, IEEE International Conference, vol. 5, 2000, pp. 3271-3276.

Linebarger et al., "Concurrency Control Mechanisms for Closely Coupled Collaboration in Multithreaded Virtual Environments", Department of Computer Science and Engineering; Lehigh University, vol. 13, 2004, 40 pages.

Sachs et al., "Virtual Visit™: Improving Communication for Those Who Need it Most", Studies in Health Technology and Informatics, vol. 94, Medicine Meets Virtual Reality 11, 2003, pp. 302-308.

Long, William F., "Robot Navigation Technology", available online at <http://www.atp.nist.gov/eao/sp950-1/helpmate.htm>, retrieved on Nov. 23, 2010, Mar. 1999, 3 pages.

Luna, Nancy, "Robot a New Face on Geriatric Care", ocregister.com, Aug. 6, 2003, 3 pages.

Mack, Michael J., "Minimally Invasive and Robotic Surgery", The Journal of the American Medical Association, vol. 285, No. 5, Feb. 7, 2001, pp. 568-572.

Mair, G. M., "Telepresence—The Technology and its Economic and Social Implications", Technology and Society, Technology and Society at a Time of Sweeping Change, Proceedings of International Symposium, Jun. 20-21, 1997, pp. 118-124.

Martin, Anya, "Brighter Days Ahead", Assisted Living Today, vol. 9, Nov./Dec. 2002, pp. 19-22.

McCardle et al., "The Challenge of Utilizing New Technology in Design Education", Loughborough University, IDATER, 2000, pp. 122-127.

Meng et al., "E-Service Robot in Home Healthcare", Proceedings of the 2000 IEEE/RSJ, International Conference on Intelligent Robots and Systems, 2000, pp. 832-837.

Metz, Cade, "HP Labs", available online at <http://www.pcmag.com/article2/0,2817,1130820,00.asp>, Jul. 1, 2003, 4 pages.

Michaud, Anne, "Introducing 'Nursebor'", available online at <http://www.cs.cmu.edu/~nursebot/web/press/globe_3_01/index.html>, retrieved on May 5, 2008, Sep. 11, 2001, 4 pages.

Microsoft Corporation, Inc., "Microsoft NetMeeting 3 Features", available online at <http://technet.microsoft.com/en-us/library/cc723477.aspx>, retrieved on Jun. 26, 2012, 2012, 6 pages.

Montemerlo, Mike, "Telepresence: Experiments in Next Generation Internet", available Online at <http://www.ri.cmu.edu/creative/archives.htm>, retrieved on May 25, 2008, Oct. 20, 1998, 3 pages.

Murphy, Robin R., "Introduction to AI Robotics", A Bradford Book, The Massachusetts Institute of Technology Press, 2000, 487 pages.

Nakajima et al., "A Multimedia Teleteaching System using an Electronic Whiteboard for Two-Way Communication of Motion Videos and Chalkboards", Robot and Human Communication, Proceedings of 2nd IEEE International Workshop, 1993, pp. 436-441.

Nakazato et al., "Group-Based Interface for Content-Based Image Retrieval", Proceedings of the Working Conference on Advanced Visual Interfaces, 2002, pp. 187-194.

Nakazato et al., "Group-Oriented User Interface for Digital Image Management", Journal of Visual Languages and Computing, vol. 14, No. 4, Aug. 2003, pp. 45-46.

Nersc, "Berkeley Lab's RAGE Telepresence Robot Captures R&D100 Award", Available online at <https://www.nersc.gov/news-publications/news/nersc-center-news/2002/berkeley-lab-s-rage-telepresence-robot-captures-r-and-d100-award/>, Retrieved on Jan. 22, 2014, Jul. 2, 2002, 2 pages.

"Nomad XR4000 Hardware Manual", Release 1.0, Nomadic Technologies, Inc., Mar. 1999, 34 pages.

North, Michael, "Telemedicine: Sample Script and Specifications for a Demonstration of Simple Medical Diagnosis and Treatment Using Live Two-Way Video on a Computer Network", Greenstar Corporation, 1998, 5 pages.

Ogata et al., "Development of Emotional Communication Robot: WAMOEBA-2R-Experimental evaluation of the Emotional Communication between Robots and Humans", Proceedings of the 2000 IEEE/RSJ International Conference on Intelligent Robots and Systems, vol. 1, 2000, pp. 175-180.

Ogata et al., "Emotional Communication Robot: WAMOEBA-2R-Emotion Model and Evaluation Experiments", Proceedings of the International Conference on Humanoid Robots, 2000, pp. 1-16.

Screenshot Showing Google Date for Lemaire Telehealth Manual, Screenshot Retrieved on Dec. 18, 2014, 1 page.

Nomadic Technologies, Inc., "Nomad Scout Language Reference Manual", Software Version: 2.7, Part No. DOC0000002, Jul. 12, 1999, 47 pages.

Office Action received for Chinese Patent Application No. 200680044698.0 on Nov. 4, 2010. (9 pages of Official Copy and 17 pages of English Translation).

Wang et al., "A Healthcare Tele-robotic System with a Master Remote Station with an Arbitrator", U.S. Appl. No. 60/449,762, filed Feb. 24, 2003, 28 pages.

Activmedia Robotics LLC, "Pioneer 2/PeopleBot™0", Operations Manual, Version 9, Oct. 2001, 78 pages.

Adams, Chris, "Simulation of Adaptive Behavior (SAB'02)—From Animals to Animats 7", Mobile Robotics Research Group, The Seventh International Conference, available online at: <http://www.dai.ed.ac.uk/groups/mrg/MRG.html>, retrieved on Jan. 22, 2014, Aug. 4-11, 2002, 1 page.

Ando et al., "A Multimedia Self-Service Terminal with Conferencing Functions", Proceedings of 4th IEEE International Workshop on Robot and Human Communication, RO-MAN'95, Jul. 5-7, 1995, pp. 357-362.

Android Amusement Corp., "Renting Robots from Android Amusement Corp!", What Marketing Secret, (Advertisement), 1982, 1 page.

Applebome, "Planning Domesticated Robots for Tomorrow's Household", New York Times, available online at <http://www.theoldrobots.com/images17/dc17.JPG>, Mar. 4,1982, 1 page.

Bar-Cohen et al., "Virtual Reality Robotic Telesurgery Simulations Using MEMICA Haptic System", Proceedings of SPIE's 8th Annual International Symposium on Smart Structures and Materials, Mar. 5-8, 2001, 8 pages.

Barrett, Rick, "Video Conferencing Business Soars as Companies Cut Travel; Some Travel Cuts are Permanent", available online at <http://www.ivci.com/international_videoconferencing_news_videoconferencing_news_19.html>, May 13, 2002, 2 pages.

Bartholomew, "Pharmacy Apothecary of England", BnF-Teaching Kit—Childhood in the Middle Ages, available online at <http://classes.bnf.fr/ema/grands/034.htm>, retrieved on Jul. 26, 2012, 2 pages.

Bauer et al., "Remote Telesurgical Mentoring: Feasibility and Efficacy", IEEE, Proceedings of the 33rd Hawaii International Conference on System Sciences, 2000, pp. 1-9.

Bauer, Jeffrey C., "Service Robots in Health Care: The Evolution of Mechanical Solutions to Human Resource Problems", BonSecours Health System, Inc., Technology Ealy Warning System, Jun. 2003, pp. 1-10.

Bischoff, Rainer, "Design Concept and Realization of the Humanoid Service Robot HERMES", In A. Zelinsky (ed.): Field and Service Robotics, Springer, London, 1998, pp. 485-492.

(56) References Cited

OTHER PUBLICATIONS

Blackwell, Gerry, "Video: A Wireless LAN Killer App?", Availabel online at <http://www.wi-fiplanet.com/columns/article.php/1010261Nideo-A-Wireless-LAN-Killer>, retrieved on Nov. 22, 2010, Apr. 16, 2002, 4 pages.
Breslow et al., "Effect of a Multiple-Site Intensive Care Unit Telemedicine Program on Clinical and Economic Outcome an Alternative Paradigm for Intensivist Staffing", Critical Care Med., vol. 32, No. 1, Jan. 2004, pp. 31-38.
Brooks, Rodney A., "A Robust Layered Control System for a Mobile Robot", IEEE, Journal of Robotics and Automation, vol. 2, No. 1, Mar. 1986, pp. 14-23.
Brooks, Rodney Allen, "Flesh and Machines: How Robots Will Change Us", available online at <http://dl.acm.org/citation.cfm?id=560264&preflayout=flat%25202%2520of>, retrieved on Nov. 23, 2010, Feb. 2002, 3 pages.
Celt et al., "The eICU: It's Not Just Telemedicine", Critical Care Medicine, vol. 29, No. 8 (Supplement), Aug. 2001, pp. 183-189.
Cheetham et al., "Interface Development for a Child's Video Conferencing Robot", Centre for Learning Technologies, Ryerson University, 2000, 4 pages.
Cleary et al., "State of the Art in Surgical Robotics: Clinical Applications and Technology Challenges", Computer Aided Surgery, Nov. 2001, pp. 1-26.
CNN, "Floating 'Droids' to Roam Space Corridors of the Future", available online at <http://edition.cnn.com/2000/TECH/space/01/12/psa/> retrieved on Nov. 11, 2010., Jan. 12, 2000, 3 pages.
CNN.com, "Paging Dr. Robot: Machine Helps Doctors with Patients", available online at <http://edition.cnn.com/2003/TECH/ptech/09/29/doctor.robot.ap/index.html>, retrieved on Sep. 30, 2003, 3 pages.
Crowley, Susan L., "Hello to Our Future", AARP Bulletin, available online at <http://www.cs.cmu.ed/-nursebot/web/press/aarp 99_14/millennium.html>, Jan. 2000, retrieved on Nov. 23, 2010, 12 pages.
Dalton, Barnaby, "Techniques for Web Telerobotics", Ph. D Thesis for degree of Doctor of Philosophy, University of Western Australia, available online at <http://telerobot.mech.uwa.edu.autinformation.html>, 2001, 243 pages.
Davies, Brian, "Robotics in Minimally Invasive Surgery", Mechatronics in Medicine Lab, Dept. Mechanical Engineering, Imperial College, London SW7 2BX, The Institution of Electrical Engineers, IEE, Savoy Place, London WC2R OBL, UK, 1995, pp. 1-2.
Davis, Erik, "Telefriend, Meet iRobot, The Smartest Webcam on Wheels", Wired Magazine, Issue 8.09, available online at <http://www.wired.com/wired/archive/8.09/irobot.html?pg=1&topic=&topic_set=>, retrieved on Jul. 7, 2012, Sep. 2000, 3 pages.
Dean et al., "1992 AAAI Robot Exhibition and Competition", Articles, AI Magazine, vol. 14, No. 1, 1993, 15 pages.
DiGiorgio, James, "Is Your Emergency Department of the Leading Edge?", Chicago Hospital News, vol. 2, No. 12, Feb. 2005, 3 pages.
Dudenhoeffer et al., "Command and Control Architectures for Autonomous Micro-Robotic Forces", FY00 Project Report, Idaho National Engineering and Environmental Laboratory, Human Systems Engineering and Sciences Department, Idaho Falls, Apr. 2001, 43 pages.
Elhajj et al., "Real-Time Haptic Feedback in Internet-Based Telerobotic Operation", IEEE International Conference on Electro/Information Technology, Jun. 2000, 10 pages.
Elhajj et al., "Supermedia in Internet-Based Telerobotic Operations", Lecture Notes in Computer Science, vol. 2216, 2001, pp. 359-372.
Elhajj et al., "Synchronization and Control of Supermedia Transmission Via the Internet", Proceedings of 2001 International Symposium on Intelligent Multimedia Video and Speech Processing, Hong Kong, May 2-4, 2001, pp. 320-323.
Ellison et al., "Telerounding and Patient Satisfaction after Surgery", American College of Surgeons, Elsevier, Inc., vol. 199, No. 4, Oct. 2004, pp. 523-530.
Evans et al., "HelpMate: The Trackless Robotic Courier", PYXIS, available online at <http://www.pyxis.com/>, 3 pages.
Fels et al., "Developing a Video-Mediated Communication System for Hospitalized Children", Telemedicine Journal, vol. 5, No. 2, 1999, 30 pages.
Fetterman, David M., "Videoconferencing Over the Internet", Qualitative Health Journal, vol. 7, No. 1, May 1966. pp. 154-163.
Fiorini et al., "Health Care Robotics: A Progress Report", IEEE International Conference on Robotics and Automation, vol. 2, Apr. 20-25, 1997, pp. 1271-1276.
Fong, Terrence, "Collaborative Control: A Robot-Centric Model for Vehicle Teleoperation",The Robotics Institute Carnegie Mellon University, Nov. 2001, 197 pages.
Gaidioz et al., "Synchronizing Network Probes to Avoid Measurement Intrusiveness with the Network Weather Service", High-Performance Distributed Computing, Proceedings of the Ninth International Symposium, 2000, pp. 147-154.
Garner et al., "The Application of Telepresence in Medicine", BT Technology Journal, vol. 15, No. 4, Oct. 1, 1997, pp. 181-187.
Ghiasi et al., "A Generic Web-based Teleoperations Architecture: Details and Experience", Proceedings of SPIE, Telemanipulator and Telepresence Technologies VI, vol. 3840, No. 234, Sep. 19, 1999, 14 pages.
Goldberg et al., "Collaborative Teleoperation via the Internet", IEEE International Conference on Robotics and Automation (ICRA), vol. 2, San Francisco, California, 2000, pp. 2019-2024.
Goldberg et al., "Desktop Teleoperation via the World Wide Web", Proceedings of IEEE International Conference on Robotics and Automation, vol. 1, May 21-27, 1995, pp. 654-659.
Goldenberg et al., "Telemedicine in Otolaryngology", American Journal of Otolaryngology, vol. 23, No. 1, Jan. 2002, pp. 35-43.
Goldman, Lea, "Machine Dreams", available online at <http://www.forbes.com/global/2002/05271043.html>, retrieved on Nov. 23, 2010., May 27, 2002, 5 pages.
Gump, Michael D., "Robot Technology Improves VA Pharmacies", U.S. Medicine Informational Central, Jul. 2001, 3 pages.
Hameed et al., "A Review of Telemedicine", Journal of Telemedicine and Telecare, vol. 5, Supplement 1, 1999, pp. 103-106.
Han et al., "Construction of an Omnidirectional Mobile Robot Platform Based on Active Dual-Wheel Caster Mechanisms and Development of a Control Simulator", Journal of Intelligent and Robotic Systems, Kluwer Acedemic Publishers, vol. 29, Nov. 2000, pp. 257-275.
Handley et al., "SDP: Session Description Protocol", RFC 2327, available Online at <http://www.faqs.org/rfcs/rfc2327.html>, retrieved on Nov. 23, 2010, Apr. 1998, 22 pages.
Hanebeck et al., "ROMAN: A Mobile Robotic Assistant for Indoor Service Applications", Proceedings of the IEEE/RSJ International Conference on Intelligent Robots and Systems, vol. 2, 1997, pp. 518-525.
"Robart I, II, III", Spawar, Systems Center Pacific, Available online at <http://www.nosc.mil/robots/land/robart/robart.html>, retrieved on Nov. 22, 2010, 1998, 8 pages.
"Using your Infrared Cell Phone Camera", Available on <http://www.catsdomain.com/xray/about.htm>, retrieved on Jan. 23, 2014, Courtesy of Internet Wayback Machine, Jan. 30, 2010, 4 pages.
Appeal from the U.S. District Court for the Central District of California in case No. 11-cv-9185, Judge Percy Anderson, Joint Appendix, vol. I of IV, Jun. 24, 2013, pp. A1-A6357.
Appeal from the U.S. District Court for the Central District of California in case No. 11-cv-9185, Judge Percy Anderson, Joint Appendix, vol. II of IV, Jun. 24, 2013, pp. A6849-A10634.
Appeal from the U.S. District Court for the Central District of California in case No. 11-cv-9185, Judge Percy Anderson, Joint Appendix, vol. III of IV, Jun. 24, 2013, pp. A10654-A15517.
Appeal from the U.S. District Court for the Central District of California in case No. 11-cv-9185, Judge Percy Anderson, Joint Appendix, vol. IV of IV, Jun. 24, 2013, pp. A15677-A18127.
Reply Brief for Defendant-Appellee VGO Communications, Inc., Appeal from the U.S. District Court for the Central District of California, in Case No. 2:11-cv-9185, Judge Percy Anderson, May 28, 2013, 75 pages.
Civil Minutes-General: Case No. CV 11-9185PA (AJWx), *InTouch Tech., Inc.* v. *VGo Commons, Inc.*, U.S. District Court for the Central District of California, Judge Percy Anderson, Sep. 10, 2012, 7 pages.

(56) References Cited

OTHER PUBLICATIONS

Defendant-Counterclaimant VGo Communications, Inc.'s Supplemental Invalidity Contentions Pursuant to the Feb. 27, 2012 Civil Minute Order, U.S. District Court for the Central District of California, Case No. CV11-9185 PA, May 14, 2012, 228 pages.

Opening Brief for Plaintiff-Appellant InTouch Technologies, Inc., Appeal from the U.S. District Court for the Central District of California in Case No. 11-cv-9185, Judge Percy Anderson, Apr. 12, 2013, 187 pages.

Reply Brief for Plaintiff—Appellant InTouch Technologies, Inc., Appeal from the U.S. District Court for the Central District of California in Case No. 11-cv-9185, Judge Percy Anderson, Jun. 14, 2013, 39 pages.

Active Media, Inc., "Saphira Software Manual", Real World, Saphira Version 5.3, 1997, 105 pages.

Apple Inc., "I Phone", iPhone Series, XP002696350, Sep. 21, 2012, pp. 1-29.

Blaer et al., "TopBot: Automated Network Topology Detection With a Mobile Robot", IEEE, Proceedings of the 2003 International Conference on Robotics and Automation, Taipei, Taiwan, Sep. 14-19, 2003, pp. 1582-1587.

Bradner, S., "The Internet Standards Process—Revision 3", Network Working Group, Request for Comments: 2026, BCP: 9, Obsoletes: 1602, Category: Best Current Practice, Oct. 1996, pp. 1-36.

Christensen et al., "BeeSoft User's Guide and Reference", Robots for the Real World™, Real World Interface, Inc ., Sep. 26, 1997, 203 pages.

Chu et al., "Detection of Target Mobile Signal Strength", Technical Development, Motorola Inc., Jan. 1999, pp. 205-206.

Dario et al., "A Robot Workstation for Diagnosis and Physical Therapy", IEEE Catalog No. 88TH0234-5, Centro "E. Piaggio" University of Pisa, Italy, 1989, pp. 67-72.

Gostai "Gostai Jazz: Robotic Telepresence", available online at <http://www.gostai.com>, 4 pages.

Leifer et al., "VIPRR: A Virtually in Person Rehabilitation Robot", Proceedings of 1997 International Conference on Rehabilitation Robotics, Apr. 14-15, 1997, 4 pages.

Minsky, Marvin, "Telepresence", OMNI Magazine, Jun. 1980, 6 pages.

Noritsugu et al., "Application of Rubber Artificial Muscle Manipulator as a Rehabilitation Robot", Mechatronics, IEEE/ASME Transactions, vol. 2, No. 4, Dec. 1997, pp. 259-267.

Osborn et al., "Quality of Life Technology Center", QoLT Research Overview: A National Science Foundation Engineering Research Center, Carnegie Mellon University of Pittsburgh, 2 pages.

Reynolds et al., "Review of Robotic Telemedicine Utilization in Intensive Care Units (ICUs)", 11th Annual ATA Symposium, Tampa, Florida, 2011, 1 page.

Tipsuwan et al., "Gain Adaptation of Networked Mobile Robot to Compensate QoS Deterioration", vol. 4, 28th Annual Conference of the Industrial Electronics Society, Nov. 5-8, 2002, pp. 3146-3151.

Tsui et al., "Exploring Use Cases for Telepresence Robots", 6th ACM/IEEE International Conference on Human-Robot Interaction (HRI), Mar. 2011, 7 pages.

UMASS Lowell Robotics Lab, "Robotics Lab @ UMASS Lowell", Department of Computer Science, Brochure, 2011, 2 pages.

Video Middleware Cookbook, "H.350 Directory Services for Multimedia", 4 pages.

U.S. Appl. No. 10/783,760, Feb. 20, 2004, 48 pages.

International Search Report for International Patent Application No. PCT/US2005/037347, Apr. 17, 2006, 2 pages.

International Preliminary Report on Patentability and Written Opinion Received for International Patent Application No. PCT/US2005/037347, Apr. 17, 2009, 7 pages.

International Preliminary Report on Patentability and Written Opinion Received for International Patent Application No. PCT/US2006/037076, Apr. 1, 2008, 6 pages.

International Search Report and Written Opinion Received for International Application No. PCT/US2006/037076, May 11, 2007, 6 pages.

International Preliminary Report on Patentability and Written Opinion Received for International Patent Application No. PCT/US/200714099, Dec. 16, 2008, 5 pages.

International Search Report Received for international Patent Application No. PCT/US2007/14099, Jul. 30, 2008, 1 page.

\* cited by examiner

Robot Face
16

Overhead Camera

REMOTE PRESENCE SYSTEM INCLUDING A CART THAT SUPPORTS A ROBOT FACE AND AN OVERHEAD CAMERA

BACKGROUND OF THE INVENTION

1. Field of the Invention

The subject matter disclosed generally relates to the field of robotic tele-presence systems.

2. Background Information

Robots have been used in a variety of applications ranging from remote control of hazardous material to assisting in the performance of surgery. For example, U.S. Pat. No. 5,762,458 issued to Wang et al. discloses a system that allows a surgeon to perform minimally invasive medical procedures through the use of robotically controlled instruments. One of the robotic arms in the Wang system moves an endoscope that has a camera. The camera allows a surgeon to view a surgical area of a patient.

There has been marketed a mobile tele-presence robot introduced by InTouch Technologies, Inc., the assignee of this application, under the trademark RP-7. The InTouch robot is controlled by a user at a remote station. The remote station may be a personal computer with a joystick that allows the user to remotely control the movement of the robot. Both the robot and remote station have cameras, monitors, speakers and microphones to allow for two-way video/audio communication. The robot camera provides video images to a screen at the remote station so that the user can view the robot's surroundings and move the robot accordingly.

InTouch also provides a system sold as VisitOR that includes a robot face that is attached to a boom. The boom and robot face can be installed into an operating room. Using a robot face in an operating room may require sterilization of the face. Additionally, the VisitOR requires the installation of a boom in the operating room. This can add to the cost and complexity of installing such a system.

BRIEF SUMMARY OF THE INVENTION

A tele-presence system that includes a cart. The cart includes a robot face that has a robot monitor, a robot camera, a robot speaker, a robot microphone, and an overhead camera. The system also includes a remote station that is coupled to the robot face and the overhead camera. The remote station includes a station monitor, a station camera, a station speaker and a station microphone.

DETAILED DESCRIPTION

Disclosed is a tele-presence system that includes a cart. The cart includes a robot face that has a robot monitor, a robot camera, a robot speaker, a robot microphone, and an overhead camera. The system also includes a remote station that is coupled to the robot face and the overhead camera. The remote station includes a station monitor, a station camera, a station speaker and a station microphone. The remote station can display video images captured by the robot camera and/or overhead camera. By way of example, the cart can be used in an operating room, wherein the overhead camera can be placed above a sterile field to provide a more advantageous vantage point to view a procedure. The user at the remote station can conduct a teleconference through the robot face and also obtain a view of a medical procedure through the overhead camera.

Figure 1:
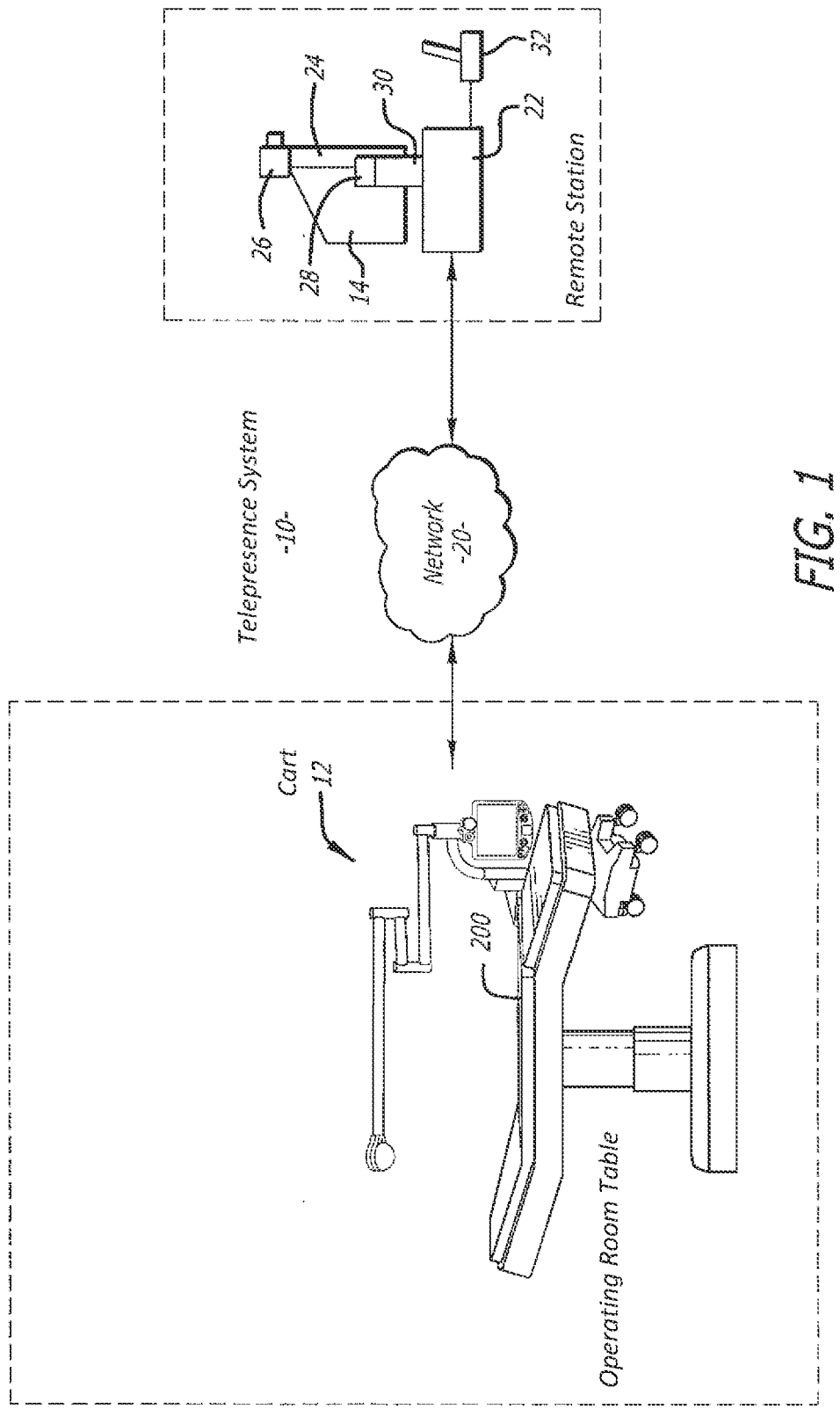
FIG. 1 is an illustration of a tele-presence system.
Figure 2:
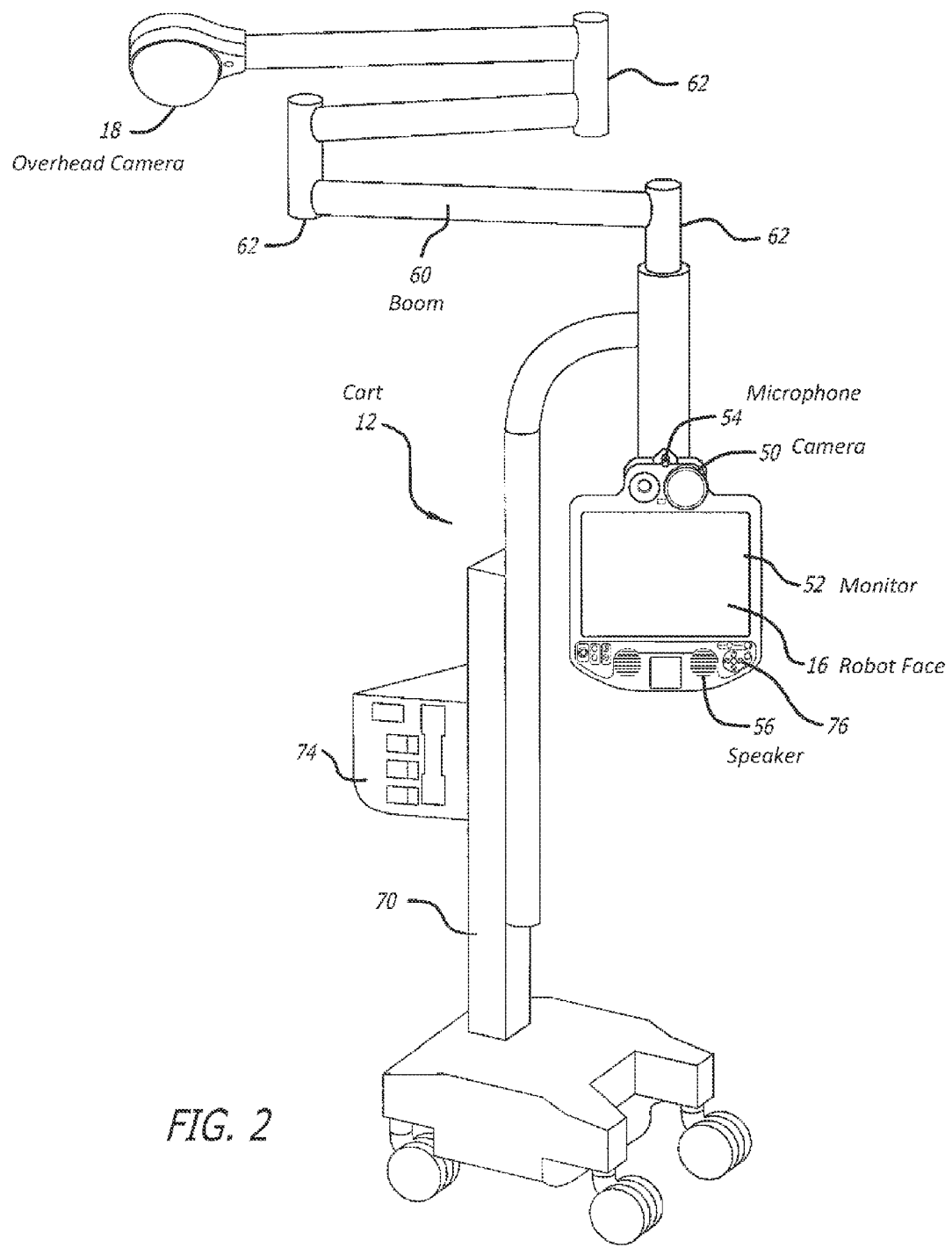
FIG. 2 is a perspective view of a cart of the system.
Figure 3:
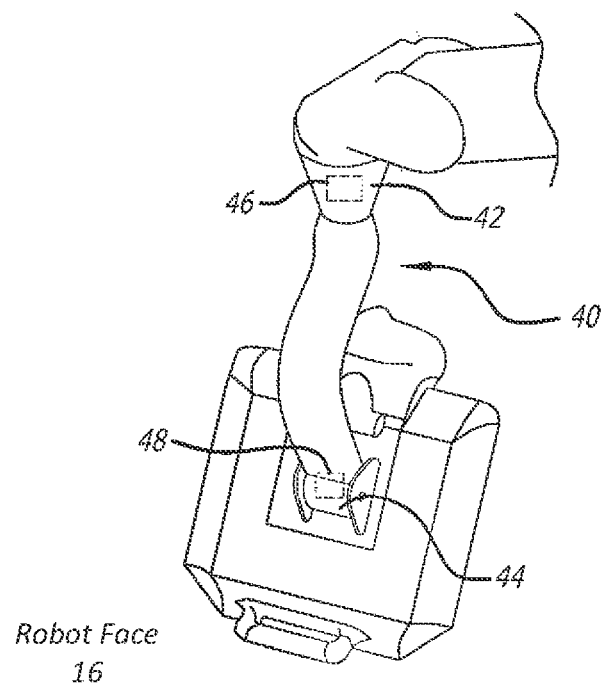
FIG. 3 is a rear view of an articulated arm and a robot face of the cart.

Referring to the drawings more particularly by reference numbers, FIGS. 1, 2 and 3 show a tele-presence system 10. The system 10 includes a cart 12 that is coupled to a remote control station 14. The cart 12 has a robot face 16 and an overhead camera 18. The remote control station 14 may be coupled to the cart 12 through a network 20. By way of example, the network 20 may be either a packet switched network such as the Internet, or a circuit switched network such as a Public Switched Telephone Network (PSTN) or other broadband system. Alternatively, the cart 12 may be coupled to the remote station 14 network thru a satellite.

The remote control station 14 may include a computer 22 that has a monitor 24, a camera 26, a microphone 28 and a speaker 30. The computer 22 may also contain an input device 32 such as a joystick or a mouse. The control station 14 is typically located in a place that is remote from the cart 12. Although only one remote control station 14 is shown, the system 10 may include a plurality of remote stations 14. In general any number of carts 12 may be coupled to any number of remote stations 14 or other carts 12. For example, one remote station 14 may be coupled to a plurality of carts 12, or one cart 12 may be coupled to a plurality of remote stations 14, or a plurality of carts 12. The system may include an arbitrator (not shown) that control access between the carts 12 and the remote stations 14.

As shown in FIG. 3, the cart 12 may include an articulated arm 40 that supports and can move the robot face 16. The articulated arm 40 may have active joints 42 and 44 that allow the robot face 16 to be panned and tilted, respectively. The active joints 42 and 44 may move in response to commands provided by the remote station. The joints 42 and 44 may contain position sensors 46 and 48, respectively, that provide positional feedback of the arm 40.

Referring to FIGS. 2 and 3, each robot face 16 includes a camera(s) 50, a monitor 52, a microphone(s) 54 and a speaker(s) 56. The robot camera 50 is coupled to the remote monitor 24 so that a user at the remote station 14 can view a video image captured by the robot camera 50. Likewise, the robot monitor 52 is coupled to the remote camera 26 so personnel at the surgical site may view the user of the remote station 14. The microphones 28 and 54, and speakers 30 and 56, allow for audible communication between the system operator and the personnel at the surgical site.

The overhead camera 18 may be coupled to a boom 60. The boom 60 may include a number of joints 62, either active or passive. The joints 62 may include positional sensors to provide feedback regarding the position of the overhead camera 18.

Figure 4:
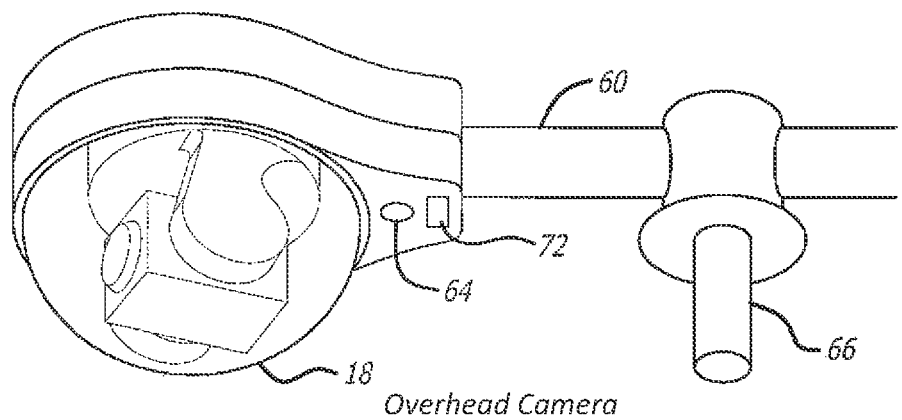
FIG. 4 is an enlarged perspective view of an overhead camera of the cart.

As shown in FIG. 4, the cart 12 may include an overhead microphone 64 and a detachable handle 66. The overhead microphone 64 may provide an alternative source of sound. The detachable handle 66 can be used to move the boom 60 and overhead camera 18. If the cart 12 is used in a sterile field, for example in an operating room, the handle 66 may be replaced with a sterile handle before each medical procedure to allow a surgeon within the sterile field to position the boom during a procedure.

Referring again to FIG. 2, the cart 12 may include a linear actuator 70 that can be remotely or locally actuated to vary the height of the robot face 16 and overhead camera 18. Varying the height allows the cart 12 to be rolled through doors and then actuated to move the face 16 and camera 18 to elevated positions. For example, the face 16 and camera 18 can be lowered to allow the cart 12 to be moved into an operating room. The camera 18 can then be raised to provide a desirable view over an operating table. The cart 12 may include a laser pointer 72 and/or directed lighting (not shown) located on the boom 60. The cart 12 may also include a local control panel 74 to move the articulated arm 40, actuator 70 and/or boom 60. The linear actuator 70 is also advantageous in moving the face 16 to be essentially at the same level as a person whether they are standing, sitting or lying in a prone position.

The robot face 16 may include a processor, hard disk drive and other circuits that enable the face 16 to function as a computer. The face 16 may include an input panel 76 that allows a user to provide input. By way of example, the operator of the remote station may provide one or more questions through the robot face 16, wherein a user of the cart provides answers through the input panel 76.

The system 10 may have certain components and software that are the same or similar to a robotic system provided by the assignee InTouch Technologies, Inc. of Goleta, Calif. under the name RP-7 and embodies a system described in U.S. Pat. No. 6,925,357, which is hereby incorporated by reference.

Figure 5:
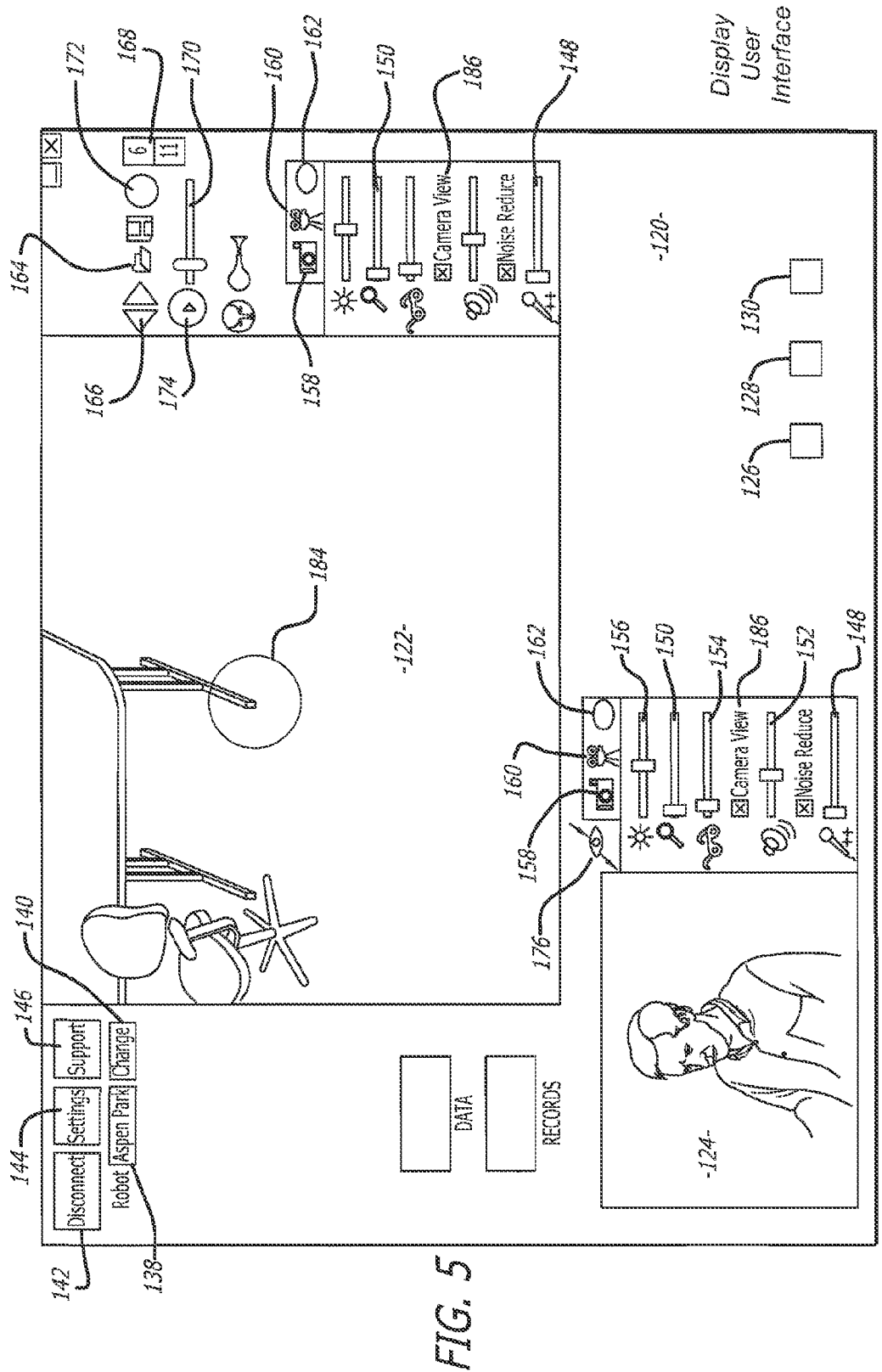
FIG. 5 is an illustration of a display user interface of a remote station.

FIG. 5 shows a display user interface ("DUI") 120 that can be displayed at the remote station 14. The DUI 120 may include a robot view field 122 that displays a video image captured by the robot camera and/or the overhead camera. The DUI 120 may also include a station view field 124 that displays a video image provided by the camera of the remote station 14. The DUI 120 may be part of an application program stored and operated by the computer 22 of the remote station 14.

Figure 6:
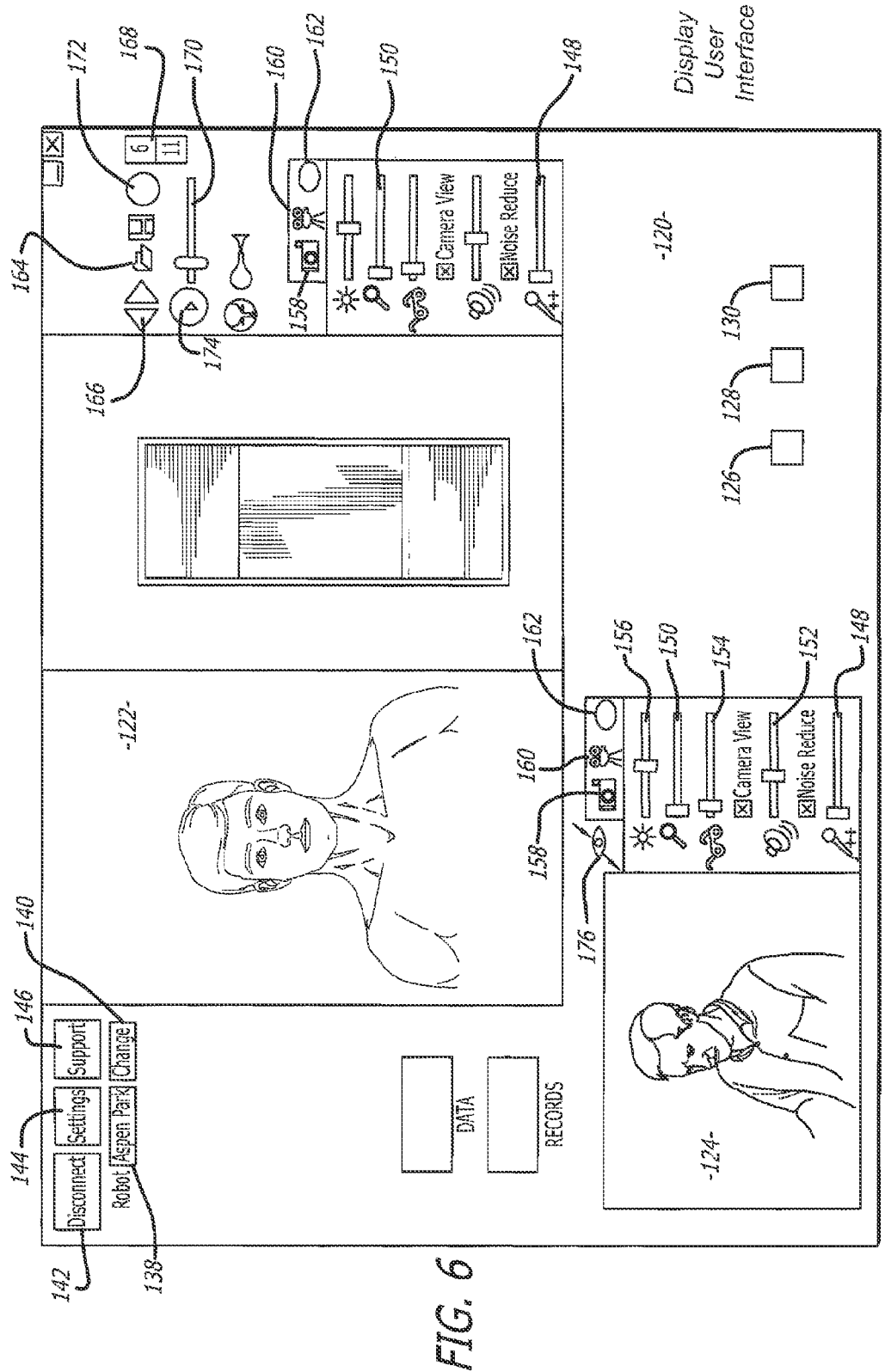
FIG. 6 is an illustration of the display user interface showing video images captured by a robot camera and an overhead camera being simultaneously displayed.

The DUI 120 may include a graphical switch 126 that allows the user to select between the video image provided by the robot camera and the video image provided by the overhead camera. The DUI 120 may also have a graphical switch 128 that allows the user to select the simultaneous display of the video images from the robot and overhead cameras as shown in FIG. 6. The video images from both cameras can be streamed to the remote station from the cart. The images can be merged by presenting a center rectangle of each image (e.g., 320×480 center area). A zoom or highlighting feature may be utilized by manipulating a cursor on either image. The system may also automatically pan a camera when the cursor is moved out of the displayed field of view.

The system may automatically present the video image from a camera that has an optimal view of an object. For example, the system may utilize pattern recognition techniques to determine which video image provides a more clear image of an object. The system may determine which camera is in closer proximity to an object and provide the image from the camera that is closer to the object. The system may utilize positional feedback from the cart to determine the proximity of the cameras relative to the object. The system may also have sensors, such as laser, sonar, etc. that can determine the proximity of the cameras to the object. The system may use the feedback and/or sensors to determine which camera is closer to an object.

The system may automatically move the cameras so that each camera is pointed to the same or substantially the same field of view. For example, if the robot face is pointed toward an object, the overhead camera can be automatically moved to capture a video image of the same object. Likewise, if the overhead camera is capturing a video image of an object, the robot face can be automatically moved to point toward the same object. This enhances the "presence" of the remote operator because they are facing the same object that the overhead camera is viewing.

The DUI 120 may have a graphical switch 130 that allows the user to switch between sound captured by the robot microphone or the overhead microphone. The system may automatically switch between microphones based on a characteristic(s) of the sound captured by the microphones. For example, the system may switch to the microphone that provides the highest aural clarity, or to the microphone that is in the closest proximity to a person or object generating the sound.

The DUI 120 may include a location display 138 that provides the location of the robot face. The CHANGE button 140 can be selected to change the default robot face in a new session. The CHANGE button 140 can be used to select and control a different robot face in a system that has multiple robot faces. The user can initiate and terminate a session by selecting box 142. The box 142 changes from CONNECT to DISCONNECT when the user selects the box to initiate a session. System settings and support can be selected through buttons 144 and 146.

Both the robot view field 122 and the station view field 124 may have associated graphics to vary the video and audio displays. Each field may have an associated graphical audio slide bar 148 to vary the audio level of a selected microphone and another slide bar 152 to vary the volume of the speakers.

The DUI 120 may have slide bars 150, 154 and 156 to vary the zoom, focus and brightness of a selected camera, respectively. A still picture may be taken at either the robot face or remote station by selecting one of the graphical camera icons 158. The still picture may be the image presented at the corresponding field 122 or 124 at the time the camera icon 158 is selected. Capturing and playing back video can be taken through graphical icons 160. A return to real time video can be resumed, after the taking of a still picture, captured video, or reviewing a slide show, by selecting a graphical LIVE button 162.

A still picture can be loaded from disk for viewing through selection of icon 164. Stored still images can be reviewed by selecting buttons 166. The number of the image displayed relative to the total number of images is shown by graphical boxes 168. The user can rapidly move through the still images in a slide show fashion or move through a captured video clip by moving the slide bar 170. A captured video image can be paused through the selection of circle 174. Play can be resumed through the same button 174. Video or still images may be dismissed from the active list through button 172. Video or still images may be transferred to the robot by selecting icon 176. For example, a doctor at the remote station may transfer an x-ray to the screen of the robot.

The system may provide the ability to annotate 184 the image displayed in field 122 and/or 124. For example, a doctor at the remote station may annotate some portion of the image captured by the robot face camera. The annotated image may be stored by the system. The system may also allow for annotation of images sent to the robot face through icon 176. For example, a doctor may send an x-ray to the robot face which is displayed by the robot screen. The doctor can annotate the x-ray to point out a portion of the x-ray to personnel located at the robot site. This can assist in allowing the doctor to instruct personnel at the robot site.

The display user interface may include graphical inputs 186 that allow the operator to turn the views of the remote station and remote cameras on and off.

Referring to FIG. 1, the cart 12 can be used in an operating room. By way of example, the boom 60 can be moved to place the overhead camera 18 above an operating table 200. The overhead camera 18 may be located above a sterile field. The robot face 16 may be placed adjacent to the sterile field. With such a configuration, personnel may conduct two-way video conferencing through the robot face 16. The overhead camera 18 may provide a more desirable view of the patient and operating procedure. This would allow a physician at the remote station to view the procedure and have a video conference to provide instructions, mentoring, etc. to personnel at the surgical site.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A tele-presence system, comprising:
    a cart, said cart includes a robot face that has a robot monitor, a robot camera, a robot speaker, a robot microphone, and an overhead camera; and,
    a remote station that is coupled to said robot face and said overhead camera, said remote station includes a station monitor, a station camera, a station speaker and a station microphone.

2. The system of claim 1, wherein said remote station can display a video image from either said robot camera or said overhead camera.

3. The system of claim 1, wherein said remote station monitor simultaneously displays a video image from said robot camera and a video image from said overhead camera.

4. The system of claim 1, wherein said remote station determines an optimal view of an object and displays a video image from said robot camera or said overhead camera, whichever provides said optimal view.

5. The system of claim 1, wherein said robot camera automatically moves to capture a video image of a field of view that is at least substantially the same as a field of view of said overhead camera.

6. The system of claim 1, wherein said overhead camera automatically moves to capture a video image of a field of view that is at least substantially the same as a field of view of said robot camera.

7. The system of claim 1, wherein said cart includes an overhead microphone.

8. The system of claim 7, wherein said remote station includes an input that allows a user to switch between said robot microphone and said overhead microphone.

9. The system of claim 7, wherein said sound generated by said station speakers is automatically switched between said robot microphone or said overhead microphone based on a characteristic of sound captured by said robot and overhead microphones.

10. The system of claim 1, wherein said cart includes an actuator that can vary a height of said robot face.

11. The system of claim 1, wherein said cart includes an articulated arm that is coupled to and can move said robot face, and a boom that is coupled to said overhead camera.

12. The system of claim 11, wherein said robot face includes an input panel and can be operated as a computer.

13. The system of claim 11, wherein said articulated arm and said boom include position sensors.

14. The system of claim 11, wherein further comprising a laser pointer attached to said boom.

15. The system of claim 11, wherein said cart boom includes a detachable handle.

16. A method for remotely viewing a field of view, comprising:
    moving a cart, the cart includes a robot face that has a robot monitor, a robot camera, a robot speaker, a robot microphone, and an overhead camera; and,
    transmitting to a remote station a video image captured by the robot camera or a video image captured by the overhead camera, the remote station includes a station monitor, a station camera, a station speaker and a station microphone.

17. The method of claim 16, wherein the video images captured by the robot and overhead cameras are both transmitted to the remote station.

18. The method of claim 17, wherein the remote station monitor simultaneously displays the video image from the robot camera and the video image from the overhead camera.

19. The method of claim 16, wherein the remote station determines an optimal view of an object and displays a video image from robot camera or the overhead camera, whichever provides the optimal view.

20. The method of claim 16, further comprising automatically moving the robot camera to capture a video image of a field of view that is at least substantially the same as a field of view of the overhead camera.

21. The method of claim 16, further comprising automatically moving the overhead camera to capture a video image of a field of view that is at least substantially the same as a field of view of the robot camera.

22. The method of claim 16, further comprising capturing sound with an overhead microphone of the cart.

23. The method of claim 22, further comprising selecting an input to switch between the robot microphone and the overhead microphone.

24. The method of claim 22, further comprising automatically switching between the robot microphone and the overhead microphone based on a characteristic of the sound captured by the robot and overhead microphones.

25. The method of claim 16, further comprising varying a height of the robot face.

26. The method of claim 25, wherein the robot face is moved in two degrees of freedom.

27. The method of claim 16, wherein the cart is moved within an operating room.

28. The method of claim 27, further comprising moving the overhead camera above a sterile field.

29. The method of claim 16, further comprising entering input into the robot face.

30. The method of claim 16, further comprising replacing a detachable handle of the cart.

* * * * *